US012163187B2

(12) United States Patent
Woodhouse et al.

(10) Patent No.: US 12,163,187 B2
(45) Date of Patent: Dec. 10, 2024

(54) METHODS OF SEQUENCING NUCLEIC ACIDS AND ERROR CORRECTION OF SEQUENCE READS

(71) Applicant: Inivata Ltd., Cambridge (GB)

(72) Inventors: Samuel Woodhouse, Cambridge (GB); Tim Forshew, Stevenage (GB); Stefanie Viola Lensing, Cambridge (GB)

(73) Assignee: INIVATA LTD., Cambridge (GB)

( * ) Notice: Subject to any disclaimer, the term of this patent is extended or adjusted under 35 U.S.C. 154(b) by 251 days.

(21) Appl. No.: 16/979,481

(22) PCT Filed: Mar. 7, 2019

(86) PCT No.: PCT/IB2019/051865
§ 371 (c)(1),
(2) Date: Sep. 9, 2020

(87) PCT Pub. No.: WO2019/180527
PCT Pub. Date: Sep. 26, 2019

(65) Prior Publication Data
US 2021/0024993 A1 Jan. 28, 2021

(30) Foreign Application Priority Data
Mar. 22, 2018 (GB) ..................... 1804641

(51) Int. Cl.
*C12Q 1/6869* (2018.01)
*C12Q 1/686* (2018.01)
(52) U.S. Cl.
CPC .......... *C12Q 1/6869* (2013.01); *C12Q 1/686* (2013.01)
(58) Field of Classification Search
CPC .................. C12Q 2563/185; C12Q 2525/101
See application file for complete search history.

(56) References Cited

U.S. PATENT DOCUMENTS

| 5,235,043 A * | 8/1993 | Collins | C12N 15/70 530/404 |
| 2012/0071331 A1 | 3/2012 | Casbon et al. | |
| 2019/0249239 A1* | 8/2019 | Glökler | C40B 20/04 |

FOREIGN PATENT DOCUMENTS

| WO | WO 2013/128281 A1 | 9/2013 |
| WO | WO 2013/142389 A1 | 9/2013 |

(Continued)

OTHER PUBLICATIONS

Devlin et al. Random Peptide Libraries: A Source of Specific Protein Binding Molecules. Science 249:404-406. (Year: 1990).*

(Continued)

*Primary Examiner* — Samuel C Woolwine
(74) *Attorney, Agent, or Firm* — James S. Keddie; Bozicevic, Field & Francis LLP

(57) ABSTRACT

Described herein, among other things, is a method of sequencing nucleic acids of interest (NAOIs). In some embodiments the method may comprise: providing a sample comprising NAOIs; attaching oligonucleotides to the NAOIs to provide labelled NAOIs, wherein the oligonucleotides comprise a PCR cycle counter generator sequence comprising at least one universal nucleotide base; amplifying the labelled NAOIs using PCR to provide an amplified library of NAOIs each containing a PCR cycle counter sequence; sequencing the amplified library of NAOIs to provide a set of sequence reads, wherein each sequence read comprises a NAOI-originating component and a PCR cycle counter component; and distinguishing true variants in NAOI sequences from false variants in NAOI sequences.

16 Claims, 5 Drawing Sheets

Specification includes a Sequence Listing.

```
                R1 sequencing primer     PCR cycle
P5 illumina adapter  binding site    counter generator   Filler region
ACACTCTTTCCCTACACGACGCTCTTCCGATCTPTKCPGKAPAKCPTKCPAKGTACG*T (SEQ ID NO:3)
                     ||||||||||||||||||||||||||||||||||||
  CTGACCTCAAGTCTGCACACGAGAAGGCTAGAAACGACTTGTCGGACGATCCATGC-phosphate(SEQ ID NO:4)
         P7 illumina      R2 sequencing primer
           adapter          binding site
```

(56) References Cited

FOREIGN PATENT DOCUMENTS

| | | |
|---|---|---|
| WO | WO 2014/071361 A1 | 5/2014 |
| WO | WO 2014/149134 A2 | 9/2014 |
| WO | WO 2014/149134 A3 | 9/2014 |
| WO | WO 2015/083004 A1 | 6/2015 |
| WO | WO 2016/118883 A1 | 7/2016 |
| WO | WO 2016/201142 A1 | 12/2016 |
| WO | WO 2017/100441 A1 | 6/2017 |
| WO | WO 2018/050722 A1 | 3/2018 |

OTHER PUBLICATIONS

Casbon et al., "A method for counting PCR template molecules with application to next-generation sequencing", Nucleic Acids Research, 2011, 39(12): e81.

Kinde et al., "Detection and quantification of rare mutations with massively parallel sequencing", PNAS, 2011, 108(23): 9530-9535.

Lubock et al., "A systematic comparison of error correction enzymes by next-generation sequencing", Nucleic Acids Research, 2017, 45(15): 9206-9217.

Reumers et al., "Optimized filtering reduces the error rate in detecting genomic variants by short-read sequencing", Nature Biotechnology, 2012, 30(1): 61-68.

Shagin et al., "A high-throughput assay for quantitative measurement of PCR errors", Scientific Reports, 2017, 7: 2718.

Tin et al., "Degenerate adaptor sequences for detecting PCR duplicates in reduced representation sequencing data improve genotype calling accuracy", Molecular Ecology Resources, 2014, 15(2): 329-336.

* cited by examiner a.

b.

a.

b.

SEQUENCE LISTING

```
<160> NUMBER OF SEQ ID NOS: 14

<210> SEQ ID NO 1
<211> LENGTH: 70
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (69)..(70)
<223> OTHER INFORMATION: A phosphorothioate linkage is present between
      nucleotides 69 and 70.

<400> SEQUENCE: 1
aatgatacgg cgaccaccga gatctacact atagcctaca ctctttccct acacgacgct    60
cttccgatct                                                           70

<210> SEQ ID NO 2
<211> LENGTH: 66
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (65)..(66)
<223> OTHER INFORMATION: A phosphorothioate linkage is present between
      the nucleotides at positions 65 and 66.

<400> SEQUENCE: 2
caagcagaag acggcatacg agatcgagta atgtgactgg agttcagacg tgtgctcttc    60
cgatct                                                               66

<210> SEQ ID NO 3
<211> LENGTH: 58
<212> TYPE: DNA
<213> ORGANISM: Artificial sequence
<220> FEATURE:
<223> OTHER INFORMATION: synthetic sequence
```

```
<220> FEATURE:
<221> NAME/KEY: misc_feature
<222> LOCATION: (34)..(34)
<223> OTHER INFORMATION: n is a universal base
<220> FEATURE:
<221> NAME/KEY: misc_feature
<222> LOCATION: (36)..(36)
<223> OTHER INFORMATION: n is a universal base
<220> FEATURE:
<221> NAME/KEY: misc_feature
<222> LOCATION: (38)..(38)
<223> OTHER INFORMATION: n is a universal base
<220> FEATURE:
<221> NAME/KEY: misc_feature
<222> LOCATION: (42)..(42)
<223> OTHER INFORMATION: n is a universal base
<220> FEATURE:
<221> NAME/KEY: misc_feature
<222> LOCATION: (46)..(46)
<223> OTHER INFORMATION: n is a universal base
<220> FEATURE:
<221> NAME/KEY: misc_feature
<222> LOCATION: (50)..(50)
<223> OTHER INFORMATION: n is a universal base
<220> FEATURE:
<221> NAME/KEY: misc_feature
<222> LOCATION: (52)..(52)
<223> OTHER INFORMATION: n is a universal base
<220> FEATURE:
<221> NAME/KEY: misc_feature
<222> LOCATION: (57)..(58)
<223> OTHER INFORMATION: A phosphorothioate linkage is present between
      the nucleotiodes at positions 57 and 58

<400> SEQUENCE: 3
acactctttc cctacacgac gctcttccga tctntncngk anakcntkcn angtacgt          58

<210> SEQ ID NO 4
<211> LENGTH: 56
<212> TYPE: DNA
<213> ORGANISM: Artificial sequence
<220> FEATURE:
<223> OTHER INFORMATION: synthetic sequence

<400> SEQUENCE: 4
cgtacctagc aggctgttca gcaaagatcg gaagagcaca cgtctgaact ccagtc           56

<210> SEQ ID NO 5
<211> LENGTH: 58
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (34)..(34)
<223> OTHER INFORMATION: n is a universal base
<220> FEATURE:
<221> NAME/KEY: misc_feature
<222> LOCATION: (36)..(36)
<223> OTHER INFORMATION: n is a universal base
<220> FEATURE:
<221> NAME/KEY: misc_feature
<222> LOCATION: (38)..(38)
<223> OTHER INFORMATION: n is a universal base
<220> FEATURE:
<221> NAME/KEY: misc_feature
<222> LOCATION: (40)..(40)
<223> OTHER INFORMATION: n is a universal base
<220> FEATURE:
<221> NAME/KEY: misc_feature
<222> LOCATION: (42)..(42)
<223> OTHER INFORMATION: n is a universal base
<220> FEATURE:
<221> NAME/KEY: misc_feature
```

```
<222> LOCATION: (44)..(44)
<223> OTHER INFORMATION: n is a universal base
<220> FEATURE:
<221> NAME/KEY: misc_feature
<222> LOCATION: (46)..(46)
<223> OTHER INFORMATION: n is a universal base
<220> FEATURE:
<221> NAME/KEY: misc_feature
<222> LOCATION: (48)..(48)
<223> OTHER INFORMATION: n is a universal base
<220> FEATURE:
<221> NAME/KEY: misc_feature
<222> LOCATION: (50)..(50)
<223> OTHER INFORMATION: n is a universal base
<220> FEATURE:
<221> NAME/KEY: misc_feature
<222> LOCATION: (52)..(52)
<223> OTHER INFORMATION: n is a universal base
<220> FEATURE:
<221> NAME/KEY: misc_feature
<222> LOCATION: (57)..(58)
<223> OTHER INFORMATION: A phosphorothioate linkage is present between
      the nucleotides at positions 57 and 58.

<400> SEQUENCE: 5
acactctttc cctacacgac gctcttccga tctntncngn anancntncn angtacgt        58

<210> SEQ ID NO 6
<211> LENGTH: 56
<212> TYPE: DNA
<213> ORGANISM: Artificial sequence
<220> FEATURE:
<223> OTHER INFORMATION: synthetic sequence

<400> SEQUENCE: 6
cgtacctagc aggctgttca gcaaagatcg gaagagcaca cgtctgaact ccagtc          56

<210> SEQ ID NO 7
<211> LENGTH: 19
<212> TYPE: DNA
<213> ORGANISM: Artificial sequence
<220> FEATURE:
<223> OTHER INFORMATION: synthetic sequence

<400> SEQUENCE: 7
ttactgaata acttaccaa                                                   19

<210> SEQ ID NO 8
<211> LENGTH: 19
<212> TYPE: DNA
<213> ORGANISM: Artificial sequence
<220> FEATURE:
<223> OTHER INFORMATION: synthetic sequence

<400> SEQUENCE: 8
ctgccggaca gcttgctag                                                   19

<210> SEQ ID NO 9
<211> LENGTH: 19
<212> TYPE: DNA
<213> ORGANISM: Artificial sequence
<220> FEATURE:
<223> OTHER INFORMATION: synthetic sequence

<400> SEQUENCE: 9
ctactggaca acttgccaa                                                   19

<210> SEQ ID NO 10
<211> LENGTH: 19
```

```
<212> TYPE: DNA
<213> ORGANISM: Artificial sequence
<220> FEATURE:
<223> OTHER INFORMATION: synthetic sequence

<400> SEQUENCE: 10
ttactggaca acttgccaa                                                  19

<210> SEQ ID NO 11
<211> LENGTH: 19
<212> TYPE: DNA
<213> ORGANISM: Artificial sequence
<220> FEATURE:
<223> OTHER INFORMATION: synthetic sequence

<400> SEQUENCE: 11
ttactggaca acttgccag                                                  19

<210> SEQ ID NO 12
<211> LENGTH: 19
<212> TYPE: DNA
<213> ORGANISM: Artificial sequence
<220> FEATURE:
<223> OTHER INFORMATION: synthetic sequence

<400> SEQUENCE: 12
ttactgaata acttaccaa                                                  19

<210> SEQ ID NO 13
<211> LENGTH: 19
<212> TYPE: DNA
<213> ORGANISM: Artificial sequence
<220> FEATURE:
<223> OTHER INFORMATION: synthetic sequence

<400> SEQUENCE: 13
ctgccggaca gcttgctag                                                  19

<210> SEQ ID NO 14
<211> LENGTH: 19
<212> TYPE: DNA
<213> ORGANISM: Artificial sequence
<220> FEATURE:
<223> OTHER INFORMATION: synthetic sequence

<400> SEQUENCE: 14
ttactggaca acttgccag                                                  19
```

METHODS OF SEQUENCING NUCLEIC ACIDS AND ERROR CORRECTION OF SEQUENCE READS

CROSS-REFERENCING

This application is a § 371 national phase of International Application No. PCT/IB2019/051865, filed on Mar. 7, 2019, which claims the benefit of United Kingdom Patent Application Serial No. GB1804641.7, filed on 22 Mar. 2018, which applications are incorporated by reference herein.

INCORPORATION BY REFERENCE OF SEQUENCE LISTING

The sequence listing entitled "INIV-011_SeqList_ST25" created on Mar. 4, 2019, and having a size of 5,101 bytes is incorporated by reference herein.

BACKGROUND

Next-generation sequencing (NGS) has inherent error and amplification biases, decreasing the ability to detect genetic alterations at an allele frequency (AF) at or below 1% and making it difficult to distinguish alterations from processing errors. Several methods have been proposed to overcome these limitations. Tagging of NGS libraries with complex molecular barcodes has been used to detect NGS errors, these methods employ a fixed length of degenerate (mixed) bases coupled to sequencing oligonucleotides that generate a high number of different tags, typically >100,000 possible combinations. Molecular barcodes are synthesized as single-stranded oligonucleotides and can be attached by PCR, ligation or primer extension. To ensure that each nucleic acid present in a sample is labelled with a unique molecular barcode, it is necessary to generate a highly complex mix of barcodes, which can be a costly and time-consuming process that requires separate barcode synthesis reactions and pooling of tags. A low diversity tag of fixed length leads to inefficient sequencing as NGS/Illumina phasing calculations cannot be made, therefore a high degree of tag diversity is required. Further methods of identifying errors involve splitting the sample into multiple replicate processing steps and identifying changes that have occurred across multiple reactions. However, splitting the reaction increases costs, complexity and in some circumstances decreases assay sensitivity. Additionally, PCR/NGS generates errors based on sequence context and thus errors are not entirely random, this can lead to consistent errors within a given sequence. Bioinformatics tools trained on control sample sets can be used to filter out consistent NGS error, however they cannot account for random errors introduced by NGS processing, e.g., by PCR. In the above methods, an error introduced during the first copy/amplification of a nucleic acid of interest (NAOI) will be propagated through the reaction and could be identified as a "true" variant/alteration, even though it was an error that occurred during the PCR.

Molecular barcoding technologies of the prior art also suffer from the disadvantage of errors occurring in an early cycle of PCR appearing as a true variation in the sequence of the underlying nucleic acid of interest, since the error will be present in the sequence read library at a high frequency. It is therefore difficult to distinguish between errors introduced during the processing and sequencing of the NAOI, and true variations, making it challenging to accurately call mutations.

Molecular barcoding of nucleic acids and other techniques for enhancing sensitivity of sequence methods are described in, for example, US20140066317, WO2015112974, WO2013142389, U.S. Pat. Nos. 8,835, 358, 8,481,292, 9,845,502 and US20140227705.

PCR counting techniques of the prior art, for example those described in Casbon et al., 2011, *Nucleic Acids Res*, 39(12):e81, allow of the number of different starting molecules in a reaction mixture to be estimated. The counter is a degenerate (mixed) base region (DBR) that is ligated to all fragments of nucleic acids during library preparation. After ligation, each fragment in the library has a unique barcode or DBR attached. These nucleic acids having a PCR counter attached (the PCR counter having a determined sequence, i.e. non-degenerate bases) are then used as the template for PCR, with each different counter sequence intending to uniquely label each starting molecule. "Counter" in this context therefore refers to counting the number of starting molecules based on the number of barcodes identified. However, such PCR "counters" do not allow daughter nucleic acids arising from different rounds of PCR to be distinguished from each other, and hence cannot count or identify the different cycles of PCR. In addition, a high complexity of different determined PCR counter sequences is required to uniquely label and subsequently identify different starting molecules.

There remains a need for simple, cost-effective methods for sequencing nucleic acids that allow for distinguishing errors in sequences introduced during PCR and/or sequencing of the nucleic acids from true variants, including identifying at what stage in the PCR amplification process errors were introduced.

SUMMARY OF THE INVENTION

In a first aspect of the invention, there is provided a method of sequencing nucleic acids of interest (NAOIs), comprising:
a. providing a sample comprising NAOIs;
b. attaching oligonucleotides to the NAOIs to provide labelled NAOIs, wherein the oligonucleotides comprise a PCR cycle counter generator sequence comprising at least one universal nucleotide base;
c. amplifying the labelled NAOIs using PCR to provide an amplified library of NAOIs each containing a PCR cycle counter sequence;
d. sequencing the amplified library of NAOIs to provide a set of sequence reads, wherein each sequence read comprises a NAOI-originating component and a PCR cycle counter component; and
e. distinguishing true variants in NAOI sequences from false variants in NAOI sequences.

False variants may be errors introduced during processing or sequencing of the NAOIs. The methods allow the skilled person to identify (or infer) errors in the sequence reads introduced during PCR or sequencing and to identify a nucleic sequence as accurately representing a parental nucleic acid fragment (and hence be a true sequence). Variants may be changes or mutations in sequence from a normal or wild-type sequence, or from a reference sequence.

The nucleic acids in the sample may be referred to as parental NAOIs since they are the template molecules used in a PCR reaction. Similarly, the amplified library comprises "daughter" NAOIs, each containing a PCR cycle counter sequence. Hence, the present invention differs from the PCR "counters" of the prior art, since the PCR cycle counter generator sequence generates a new PCR cycle counter sequence each time the labelled parental strand is copied during sequential cycles of PCR. The PCR cycle counter generator sequence may also be referred to as a PCR cycle tracer or PCR cycle tracker, since it allows molecules arising from different rounds of PCR to be distinguished from each other, which is a unique feature of the present invention.

Methods of the invention may be combined with a method that uniquely tags different starting molecules in the pool of parental NAOIs, for example in molecular barcoding techniques. In a second aspect of the invention, there is therefore provided a method of sequencing nucleic acids of interest (NAOIs), comprising:
  a. providing a sample comprising NAOIs;
  b. attaching oligonucleotides to the NAOIs to provide labelled NAOIs, wherein the oligonucleotides comprise a PCR cycle counter generator sequence comprising at least one universal nucleotide base and a molecular barcode;
  c. amplifying the labelled NAOIs using PCR to provide an amplified library of NAOIs each containing a PCR cycle counter sequence and a barcode sequence;
  d. sequencing the amplified library of NAOIs to provide a set of sequence reads, wherein each sequence read comprises a NAOI-originating component, a PCR cycle counter component and a barcode component; and
  e. distinguishing true variants in NAOI sequences from false variants in NAOI sequences.

In a third aspect of the invention, there is provided a double stranded oligonucleotide comprising a first and a second strand, the first strand comprising a PCR cycle counter generator sequence, optionally a molecular barcode, a sequencing adaptor, a universal priming site and/or filler region, and a ligation moiety at its 3' end, and the second strand comprising a region complementary to the PCR cycle counter generator sequence, optionally a molecular barcode, a sequencing adaptor, a universal priming site and/or filler region, and a ligation moiety at its 5' end. Pools of such oligonucleotides are also provided.

In a fourth aspect of the invention there is provided a method of error correcting nucleic acid sequence reads, comprising:
  a. providing a dataset comprising a plurality of sequence reads from a sample, each sequence read comprising a NAOI-originating component and a PCR cycle counter component and optionally a barcode component;
  b. grouping sequence reads by the sequence of the PCR cycle counter, the NAOI-originating component and/or the barcode component; and
  c. correcting errors in the sequence reads, if necessary, to provide a consensus (i.e. an error-corrected sequence) sequence for each originating nucleic acid of interest.

In a fifth aspect of the invention there is provided a method, comprising:
  a. providing a sample from a patient, said sample comprising one or more NAOIs; and
  b. sequencing one or more NAOIs according to a method of the invention.

The method may be a method of diagnosing cancer, a method of determining cancer prognosis, a method of determining cancer remission or relapse, a method of characterising cancer, a method of detecting progression of cancer, or a method of determining the presence or absence of residual cancer. The method may comprise extracting, isolating or enriching for the NAOI from the patient sample prior to sequencing the one or more NAOIs.

In a sixth aspect of the invention there is provided a method of treating a disease, such as cancer, comprising
  a. providing a sample from a patient, said sample comprising one or more cell-free nucleic acid molecules of interest (NAOI);
  b. sequencing one or more NAOIs according to a method of the invention; and
  c. administering a therapy to the patient, such as a cancer therapy.

In a seventh aspect of the invention there is provided a method of determining a treatment regimen for a patient, such as a cancer patient or a patient suspected of having cancer, comprising:
  a. providing a sample from a patient, said sample comprising one or more cell-free nucleic acid molecules of interest (NAOI);
  b. sequencing one or more NAOIs according to a method of the invention; and
  c. selecting a treatment regimen for the patient according to the sequence or sequences of the one or more NAOIs.

The method may further comprise administering said treatment regimen to the patient.

In an eighth aspect of the invention there is provided a method of predicting a patient's responsiveness to a cancer treatment, comprising
  a. providing a sample from a patient, said sample comprising one or more cell-free nucleic acid molecules of interest (NAOI);
  b. sequencing one or more NAOIs according to a method of the invention;
  c. predicting a patient's responsiveness to a cancer treatment according to the sequence or sequences of the one or more NAOIs.

In a further aspect of the invention there is provided a kit of parts, comprising a pool of oligonucleotides of the invention, and optionally instructions for use. The instructions may be for a method of the invention as described herein.

In any embodiment, a true variant (as opposed to a false variant) can be identified by: (i) grouping the sequence reads for a potential variant based on fragmentation breakpoints and/or a unique molecular identifier and/or a non unique molecular identifier; (ii) for each group established in (i), counting the number of PCR cycle counter sequences; and (ii) calling a potential variant as a true variant if a group is associated with multiple PCR cycle counter sequences. This method may involve identifying a group as being associated with multiple PCR cycle counter sequences and calling the potential variant associated with that group as a true variant.

BRIEF DESCRIPTION OF THE FIGURES

The skilled artisan will understand that the drawings, described below, are for illustration purposes only. The drawings are not intended to limit the scope of the present teachings in any way.

DETAILED DESCRIPTION OF THE INVENTION

Figure 1:
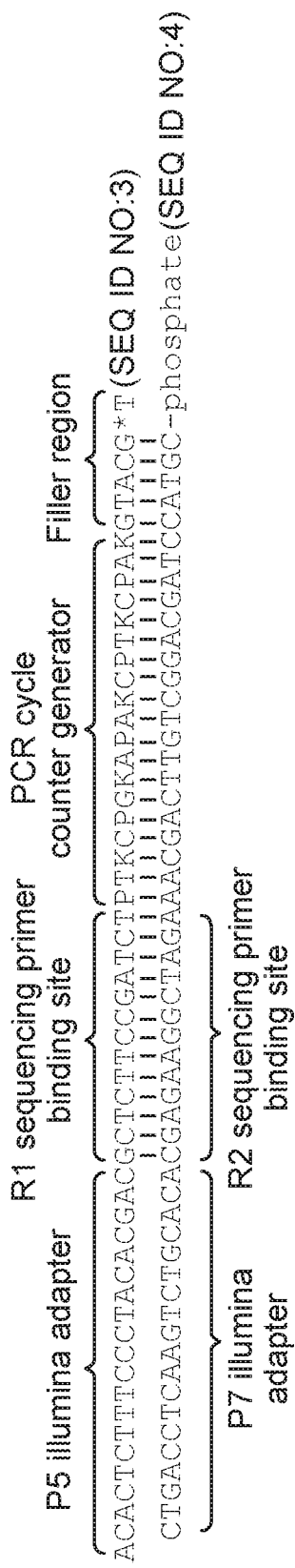
FIG. 1 depicts an example oligonucleotide of the invention. The PCR cycle counter generator sequence is followed by a filler region that facilitates ligation of the adapter. * represents a phosphorothioate linkage. A phosphorothioate bond stops the adapter being digested by enzymes that have exonuclease activity. The phosphate group is present as a ligation moiety. K indicates the universal base dK and P indicates the universal base dP.
Figure 2:
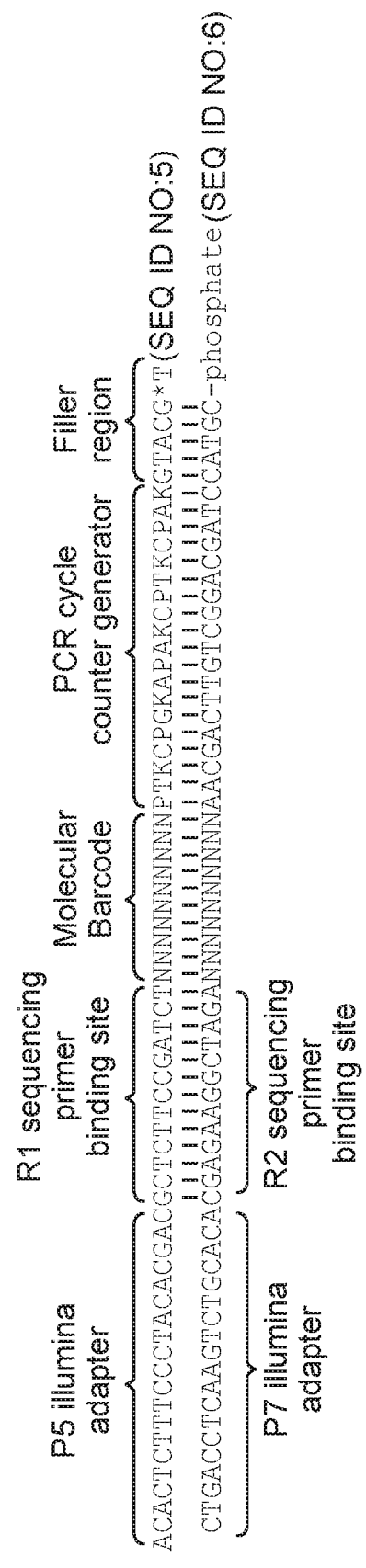
FIG. 2 depicts a further example of an oligonucleotide of the invention. This version includes a molecular barcode sequence. The PCR cycle counter generator sequence is followed by a filler region that facilitates ligation of the adapter. * represents a phosphorothioate linkage. A phosphorothioate bond stops the adapter being digested by enzymes that have exonuclease activity. The phosphate group is present as a ligation moiety.
Figure 3:
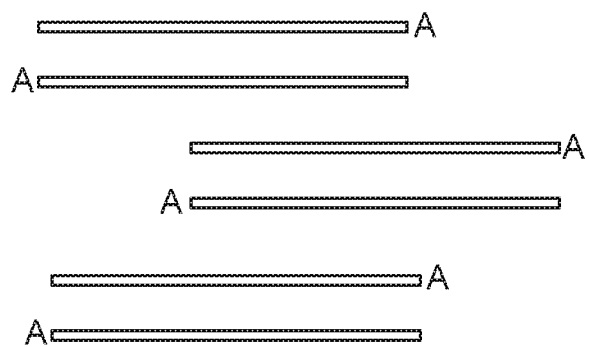
FIG. 3 shows an example workflow with a PCR cycle counter. A. DNA molecules are end repaired and A-tailed. B. Adapters are ligated, these contain the Illumina adapter sequences as well as the PCR cycle counter generator sequence. C. Represents DNA molecules with the same insert sequence following PCR amplification (4 cycles) and sequencing. D. 5 different PCR cycle counters identify the same base change. As only 4 cycles of PCR were performed, more than one parent molecule contains this identified variant, allowing the variant to be called as true.
Figure 3:
Figure 3:
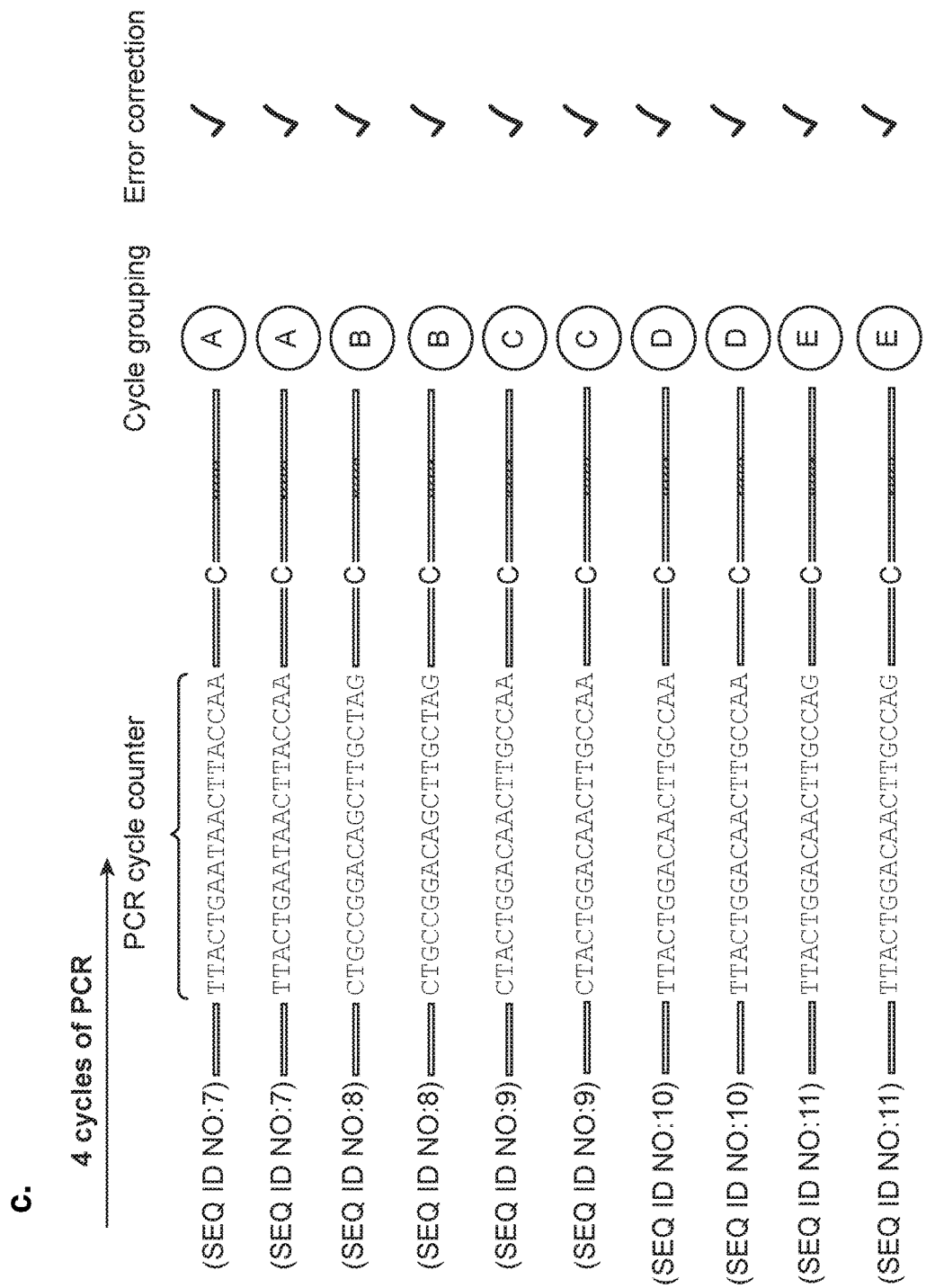
Figure 4:
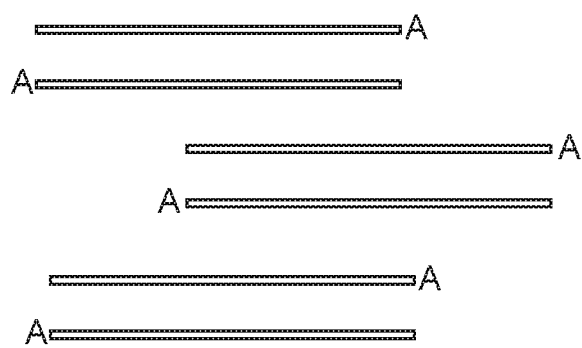
FIG. 4 shows an example workflow with a PCR cycle counter. A. DNA molecules are end repaired and A-tailed. B. Adapters are ligated, these contain the Illumina adapter sequence, a molecular barcode sequence as well as the PCR cycle counter generator sequence. C. Represents a single DNA molecule following PCR amplification and sequencing. The molecular barcode as well as the sequence of the NAOI can be used to identify molecules that originate from the same starting molecule. PCR amplification has given the daughter molecules numerous PCR counter sequences which can be used to group the reads. A base change can occur in the majority of reads but if it only occurs in one PCR counter family it is a PCR or sequencing error and can thus be eliminated.
Figure 4:
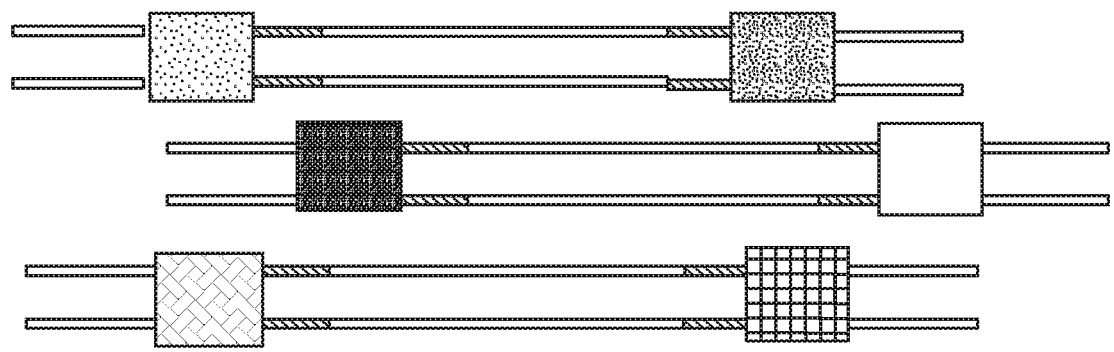
Figure 4:
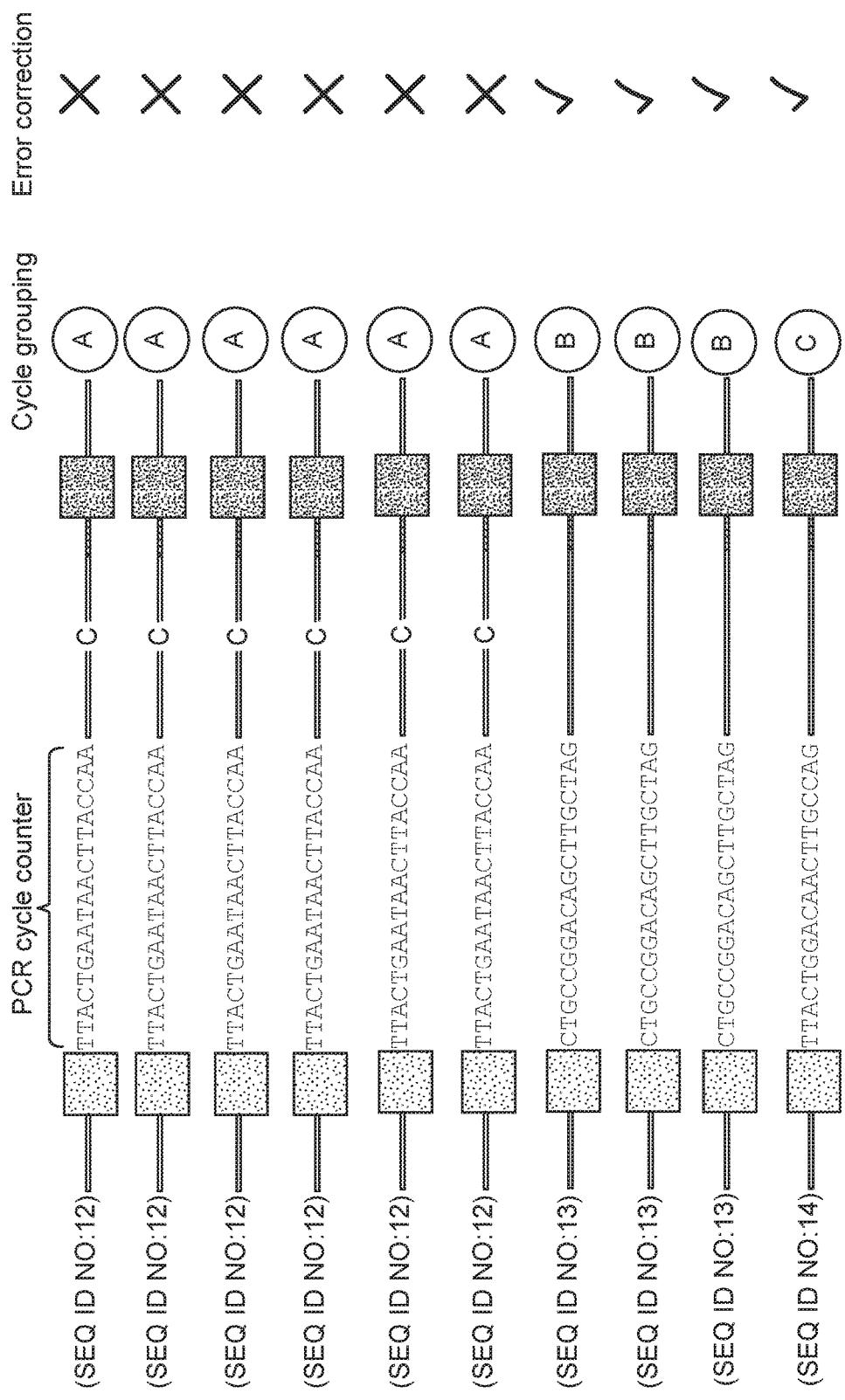

The present invention provides new methods to help identify true variations in nucleic acid sequences and to distinguish them from errors introduced during the amplification or sequencing of the nucleic acid. The variations being detected may be changes in nucleic acid sequence from a healthy or wild type sequence, or from a reference sequence. The methods employ a PCR cycle counter generator, which is an oligonucleotide comprising universal bases that is attached to a nucleic acid of interest to be sequenced. The nucleic acid of interest so labelled with the PCR cycle counter generator provides a new sequence in each new cycle of PCR. Each new sequence comprises a component arising from the starting NAOI molecule and a component arising from the PCR cycle counter generator, specifically the complement of the starting NAOI and the attached PCR cycle counter generator. Since the molecule having the PCR cycle counter generator attached is present in the PCR reaction, each round of PCR has the capacity to produce a new PCR cycle counter sequence for each labelled NAOI. The resulting sequence reads provide valuable information regarding the point at which daughter molecules were generated in the PCR reaction, enabling error correction of the NAOI sequence to be conducted.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms may be defined below for the sake of clarity and ease of reference.

The PCR cycle counter generators can be combined with molecular barcoding technologies (or indeed other techniques that allow starting molecules to be uniquely labelled or distinguished from each other) to further improve the sensitivity of the method for detecting true variants. Such methods may comprise a step of grouping sequence reads to group together all sequence reads arising from the same starting molecule.

In one embodiment of the invention, the method comprises:
  a. providing a sample comprising parental NAOIs;
  b. attaching oligonucleotides to the parental NAOIs to provide labelled parental NAOIs, wherein the oligonucleotides comprise a PCR cycle counter generator sequence comprising at least one universal nucleotide base;

c. amplifying the labelled parental NAOIs using PCR to provide an amplified library of daughter NAOIs each containing a PCR cycle counter sequence;
d. sequencing the amplified library of daughter NAOIs to provide a set of sequence reads, wherein each sequence read comprises a NAOI-originating component and a PCR cycle counter component; and
e. distinguishing true variants in parental NAOI sequences from false variants in parental NAOI sequences.

Samples

The NAOIs may be contained in or derived from a sample from a patient. In some embodiments, the sample is a biological sample obtained from a subject, or a sample containing nucleic acid of interest that is extracted from a biological sample obtained from a subject. The sample can be a tissue sample, for example a surgical sample. Preferably the sample is a liquid biopsy sample, such as blood, plasma, serum, urine, seminal fluid, stool, sputum, pleural fluid, ascetic fluid, synovial fluid, cerebrospinal fluid, lymph, nipple fluid, cyst fluid, or bronchial lavage. In some embodiments the sample is a cytological sample or smear or a fluid containing cellular material, such as cervical smear, nasal brushing, esophageal sampling by a sponge (cytosponge), endoscopic/gastroscopic/colonoscopic biopsy or brushing, cervical mucus or brushing.

Many of the above samples can be obtained non-invasively and can therefore be taken regularly without significant risk or discomfort to the subject. Methods of the invention may comprise a step of obtaining a sample from a patient. Alternatively, the methods may be carried out on samples previously obtained from a patient (i.e., ex vivo/in vitro methods). In one embodiment of the invention, samples and/or NAOIs of interest are obtained by dialysis.

Samples may be obtained from patients suspected of having a particular disease or condition, such as cancer. Such a disease or condition can be diagnosed, prognosed, monitored and therapy can be determined based on the methods, systems and kits described herein. Samples may be obtained from humans or from animals, such as a domesticated animal, for example a cow, chicken, pig, horse, rabbit, dog, cat, or goat. Usually, a sample will be derived from a human.

To obtain a blood sample, any technique known in the art may be used, e.g., a syringe or other vacuum suction device. A blood sample can be optionally pre-treated or processed prior to tagging and analysis. Examples of pre-treatment steps include the addition of a reagent such as a stabiliser, a preservative, a fixant, a lysing reagent, a diluent, an anti-apoptotic reagent, an anti-coagulation reagent, an anti-thrombotic reagent, magnetic property regulating reagent, a buffering reagent, an osmolality regulating reagent, a pH regulating reagent, and/or a crosslinking reagent. In addition, plasma may be obtained from the blood sample, and the plasma be used in the subsequent analysis. A blood sample may be processed to remove cells to obtain plasma, for example by centrifugation and/or filtration.

When obtaining a sample from a human or an animal (e.g., blood sample), the amount can vary depending upon human or animal size and the condition being screened. In some embodiments, up to 50, 40, 30, 20, 10, 9, 8, 7, 6, 5, 4, 3, 2, or 1 mL of a sample is obtained. In some embodiments, 1-50, 2-40, 3-30, or 4-20 mL of sample is obtained. In some embodiments, more than 5, 10, 15, 20, 25, 30, 35, 40, 45, 50, 55, 60, 65, 70, 75, 80, 85, 90, 95 or 100 mL of a sample is obtained.

In particular embodiments of the invention, the method comprises a step of obtaining the sample from a patient. In other embodiments, the sample or NAOI is simply provided, as a sample was obtained at a prior point in time. The skilled person is aware of suitable techniques for obtaining, storing, stabilising and/or transporting samples prior to analysis.

A sample may be processed prior to undergoing analysis. Such processing steps may comprise purification (for example removal of cells and/or debris from the sample) or extraction or isolation of the NAOI from the sample. In one embodiment, processing of the sample comprises:
a) purification of the sample to obtain a purified sample comprising the nucleic acid of interest;
b) extraction or isolation of the nucleic acid of interest from the patient sample; and/or
c) enrichment of the sample for the NAOI.

In the case of, for example, blood samples, the NAOI may be extracted from the blood sample for analysis. The amount of nucleic acid present in the extracted sample may also be quantified prior to analysis.

Possible methods to purify the sample include centrifugation. Possible extraction methods include, for example, magnetic-bead-based extraction or silica-membrane-based extraction. Purification or extraction methods will also act to enrich the sample for the NAOI, or further, separate, steps may be taken to enrich the sample. The sample may also be processed during the course of the method to remove unwanted components, for example purification of a reaction mixture comprising NAOIs having one or more oligonucleotides attached to remove un-ligated oligos. Suitable and appropriate methods of purification will be familiar to the skilled person.

The sample might not always be a patient sample, but instead could be a sample obtained from the environment, for example when testing for the presence or absence of nucleic acids, such as microbial nucleic acids. The present invention is therefore useful in detecting viruses, bacteria and fungi, for example from a sample (such as a swab) obtained from a surface. The invention can also be used to test liquids, such as water supplies.

The human or animal patient, or sample obtained from the environment, can be tested for a variety of diseases and conditions using the invention, for example cancer, infection or genetic disorders.

Cancers include acute lymphoblastic leukemia, acute or chronic lymphocytic or granulocytic tumor, acute myeloid leukemia, acute promyelocytic leukemia, adenocarcinoma, adenoma, adrenal cancer, basal cell carcinoma, bone cancer, brain cancer, breast cancer, bronchi cancer, cervical dysplasia, chronic myelogenous leukemia, colon cancer, epidermoid carcinoma, Ewing's sarcoma, gallbladder cancer, gallstone tumor, giant cell tumor, glioblastoma multiforma, hairy-cell tumor, head cancer, hyperplasia, hyperplastic corneal nerve tumor, in situ carcinoma, intestinal ganglioneuroma, islet cell tumor, Kaposi's sarcoma, kidney cancer, larynx cancer, leiomyomater tumor, liver cancer, lung cancer, lymphomas, malignant carcinoid, malignant hypercalcemia, malignant melanomas, marfanoid habitus tumor, medullary carcinoma, metastatic skin carcinoma, mucosal neuromas, mycosis fungoide, myelodysplastic syndrome, myeloma, neck cancer, neural tissue cancer, neuroblastoma, osteogenic sarcoma, osteosarcoma, ovarian tumor, pancreas cancer, parathyroid cancer, pheochromocytoma, polycythemia vera, primary brain tumor, prostate cancer, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor.

Infections include bacterial, viral, fungal and parasitic infections. Bacterial infections include *Bacillus, bartonella, Bordetella, borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio* and *Yersinia* infections. Viral infections include alphavirus, enterovirus, flavivirus, hepatitis A virus, hepatitis B virus, hepatitis C virus, hepatitis E virus, deltavirus, cytomegalovirus, herpes virus, lentivirus, dengue virus, Epstein-Barr virus, HIV, HPV, pneumovirus, influenza virus, arenavirus, norovirus, morbillivirus, cardiovirus, rubulavirus, rabies virus, rotavirus, rubella virus, Venezuelan equine encephalitis virus, western equine encephalitis virus, west nile virus, yellow fever virus and zika virus infections. Fungal infections include athlete's foot (*Tinea pedis*), nail infections (*Tinea unguium*), ringworm, intertrigo, pituriasis *versicolor* (Tinea *versicolor*) infections and thrush (*Candida albicans*). Parasitic infections include *Entamoeba histoloitica, Giardia lamblia, Cryptosporidium parvum, Trichomonas vaginalis, Plasmodium malariae, Toxoplysma gondii, Pneumocystis jiroveci, Trypanosoma cruzi, Trypanosoma gambiense, Leishmania donovani, Diphyllobothrium latum, Echinococcus granulosus, Taenia saginata, Taenia solium, Schistosoma mansoni, Clonorchis sinensis, Paragonimus westermani, Ancylostoma duodenale, Ascaris lumbricoides, Enterobius vermicularis, Strogyloides stercoralis, Trichinella spi rallis, Trichuris trichiura, Dracunculus medineinsis, Loa loa, Onchocerca volvulus, Wuchereria bancrofti, Toxocara canis, Pediculus humanus, Dermetobia huminis, Sarcoetes scabiei, Dermacentor* and *Latrodectus mactans* infections.

Genetic disorders include 22q11.2 deletion syndrome, Angelman syndrome, Canavan disease, Charcot-Marie-Tooth disease, Cri du chat, cystic fibrosis, Down's syndrome, Duchenne muscular dystrophy, haemochromatosis, haemophilia, Klinefelter syndrome, neurofibromatosis, phenylketonuria, polycystic kidney disease, Prader-Willi syndrome, sickle-cell disease, spinal muscular atrophy, Tay-Sachs disease and Turner syndrome. Of particular relevance is Down's syndrome and other aneuploidies, as the present invention can be used to detect such diseases in a sample obtained from a pregnant female, in particular a blood sample comprising cell-free fetal DNA (non-invasive prenatal testing, NIPT).

Methods of the invention can be carried out more than once to minimise false positives or negatives. In preferred embodiments, the methods of the invention are carried out on two or more samples (for example samples derived from a patient), or a sample is split into two or more test samples (prior to or after processing of the sample) and the methods are carried out on the two or more test samples. This greatly increases the specificity of the methods. When the methods are repeated in this way, the method may comprise comparing the analysis from the two samples or two test samples.

The NAOIs

The NAOI may be at least 25 base pairs in length. In some embodiments, the NAOI may be from 25 to 100,000 base pairs in length, from 25 to 50,000 base pairs in length, from 25 to 10,000 base pairs in length, from 25 to 1000 base pairs in length, from 50 to 500 base pairs in length in length, from 100 to 250 base pairs in length, or from 100 to 200 base pairs in length. In order for the NAOI to be labelled and sequenced, the NAOI may be fragmented to an appropriate size (for example between 100 and 200 base pairs in length). Indeed, the NAOI may be an entire genome that is fragmented to an appropriate length to allow labelling and sequencing to take place. As discussed above, the NAOI may be from any suitable source, including a human, plant or microbial source, depending on the method being undertaken. Most commonly, the NAOI will be a human NAOI. A sample comprising NAOIs may comprise a mixture of NAOIs from a plurality of different sources.

In one embodiment, the NAOI is up to 50,000, up to 10,000, up to 5,000, up to 1,000, up to 500, up to 300, up to 250, up to 200, up to 180, up to 160, up to 140, up to 120, up to 100, up to 80, or up to 75 nucleotides in length. In one embodiment, the NAOI is from about 10 to about 10,000 nucleotides, about 10 to about 5,000 nucleotides, about 10 to about 3,000 nucleotides, about 10 to about 1,500 nucleotides about 10 to about 800 nucleotides about 10 to about 600 nucleotides about 10 to about 300 nucleotides, about 50 to about 250 nucleotides, about 100 to about 200 nucleotides, or about 100 to about 150 nucleotides in length.

The NAOI may be single stranded or double stranded. The NAOI may be a viral nucleic acid, microbial nucleic acid or genomic nucleic acid.

The NAOI can be DNA, RNA or cDNA. In one embodiment, the NAOI may be DNA obtained by reverse transcriptase of RNA. Accordingly, the method may comprise converting an RNA sequence to a DNA sequence to obtain the NAOI, optionally using a reverse transcriptase.

The NAOI may be a cell-free DNA (cfDNA), in particular a circulating tumour DNA (ctDNA) or circulating foetal DNA (cfDNA). Of course, ctDNA is of particular interest in embodiments relating to cancer diagnosis, prognosis or treatment. cfDNA is of particular interest in embodiment relating to non-invasive prenatal testing (NIPT).

The Oligonucleotides

The NAOIs (or sample comprising them) are contacted with a pool of oligonucleotides that are subsequently attached to the NAOIs. The oligonucleotides that are attached to the NAOIs comprise at least one universal base as a PCR cycle counter generator sequence. The oligonucleotide may be single or double stranded. Single-stranded oligonucleotides may be in the form of a stem loop or hairpin loop, or may have a tertiary structure, to increase stability of the molecule. Preferably the oligonucleotides are double stranded.

The oligonucleotides may further comprise a molecular barcode and a sequencing adaptor. Both are well known in the art. The sequencing adaptor may be an asymmetric sequencing adaptor (having a complementary section and a non-complementary section). The sequencing adaptor may be partial sequencing adaptors. The sequencing adaptors may incorporate universal priming sites and/or sequencing primer sites into the NAOI.

Usually the oligonucleotide will comprise a combination of universal and non-universal bases. For example, for double-stranded oligonucleotides, the presence of non-universal base pairs in the first strand increases the stability of the molecule as it promotes hybridisation of the two strands together. Similarly, for single-stranded oligonucleotides, such as those in a hairpin or stem loop formation, the presence of non-universal base pairs increases the stability of the molecule as it promotes hybridisation between the complementary parts of the molecule.

"Non-universal nucleotide base" and "non-universal base" refer to nucleotide bases that only pair with one type of base under stringent conditions, or has a strong preference for only one type of base. Non-universal bases include the standard "natural" bases A, T, C, G and U. The IUPAC system of nomenclature is used herein, and nucleobases are represented by the first letters of their chemical names: A (Adenine), T (Thymine), C (Cytosine), G (Guanine) and U (Uracil). Other non-universal bases beyond the standard bases that may be included in the oligonucleotide include unnatural base pairs (UBPs) such as 5-methylcytosine, 5-hydroxymethylcytosine, hypoxanthine, xanthine, 7-methylguanine and 5,6-dihydrouracil.

"Universal nucleotide base" and "universal base" refer to bases that are able to hybridise to more than one type of nucleotide (i.e. at least two different types/species of nucleotides) under stringent conditions. For example, a universal base may be able to base pair with each or a subset of the natural DNA bases with little or no discrimination between them. Therefore, the use of universal bases allows nucleotides to be incorporated randomly (or semi-randomly, depending on the reaction conditions and/or annealing preferences of the universal base) to generate a random PCR cycle counter sequence.

In the case of double stranded oligonucleotides, either one or both strands of the oligonucleotide may comprise universal bases. In some embodiments, the oligonucleotide (for example a first strand of a double stranded oligonucleotide) may comprise at least 1, 2, 3, 4, 5, 6, 7, 8, 9, 10, 11 or at least 12 universal bases. In one embodiment, the oligonucleotide (for example a first strand of a double stranded oligonucleotide) may comprise from 1 to 20 universal bases, or from 2 to 8 universal bases. Usually, the oligonucleotide will have a first strand that comprises the universal bases and a second strand that does not comprise universal bases.

Stringent hybridising conditions are known to the skilled person, and are chosen to reduce the possibility of non-complementary hybridisation. Examples of suitable conditions are disclosed in Nucleic Acid Hybridisation: A Practical Approach (B. D. Hames and S. J. Higgins, editors IRL Press, 1985). For example, stringent hybridisation conditions include an aqueous environment containing about 30 mM magnesium sulfate, about 300 mM Tris-sulfate at about pH 8.9, and about 90 mM ammonium sulfate at about 60-68° C., or equivalents thereof.

A universal base may pair indiscriminately in any sequence context, or at least does not have a strong preference for a particular type of base under stringent conditions. Thus, unlike the bases A, T, C, G and U, universal bases pair with more than one other type of base, in particular under stringent conditions. The universal base may be selected from the group consisting of 2'-deoxyinosine (inosine) and derivatives thereof, nitroazole analogues and derivatives thereof, hydrophobic aromatic non-hydrogen-bonding bases and derivatives thereof, 3'-nitropyrrole bases and derivatives thereof (for example 3'-nitropyrrole CE phosphoramidite), nitroindole bases and derivatives thereof (for example 4-, 5- and 6-nitroindole CE phosphoramidite and 5-nitroindole-3-carboxamide), 2'-deoxynucleoside and derivatives thereof, K-2'-deoxyribose (dK), P-2'-deoxyribose (dP), 2'-deoxyisoguanine and 2'-deoxynebularine. In one embodiment, the universal base is selected from the group consisting of K-2'-deoxyribose and P-2'-deoxyribose. The oligonucleotide may comprise a single type of universal base (such as K-2'-deoxyribose), or the oligonucleotide may comprise a mixture of more than one type of universal base. "Type" in this context refers to the specific species of universal base, for example each of 2'-deoxyinosine (inosine), 3'-nitropyrrole CE phosphoramidite, 4-, 5- and 6-nitroindole CE phosphoramidite and 2'-deoxynucleoside are all different types (or "species") of universal base.

Universal base analogues with no or little pairing bias and no alteration in stability are reviewed in Loakes D. (2001) Survey and summary: The applications of universal DNA base analogues. Nucleic Acids Res, 29(12): 2437-2447, the contents of which are incorporated by reference herein. The degenerate bases dP and dK are further described in P. Kong Thoo Lin. and D. M. Brown, Nucleic Acids Res., 1989, 17, 10373-10383 and P. Kong Thoo Lin. and D. M. Brown, Nucleic Acids Res., 1992, 20, 5149-5152.

When universal bases such as nitroindole and 5-nitroindole-3-carboxamide are used, it may be necessary to use existing and bespoke polymerases that are able to incorporate dNTPs and extend across such types of universal base (as discussed in, for example, Loakes, et al (2009) J Am Chem Soc. 131(41) Evolving a polymerase for hydrophobic base analogues). When using universal bases such as K-2'-deoxyribose and P-2'-deoxyribose, it may be necessary to use polymerases that have an inactivated uracil binding pocket in order to allow strand extension across such universal bases (e.g. KAPA HiFi HotStart Uracil+ ReadyMix, VeraSeq Ultra, Phusion U Hotstart DNA Polymerase); or polymerases that lack proof reading activity such as taq.

The presence of the one or more universal bases in the oligonucleotide provides the PCR cycle generator sequence, since each round of PCR amplification has the capacity to generate a new PCR cycle counter sequence in the daughter molecules. The total number of sequence reads for a given PCR cycle counter can therefore be used as an indicator of the point at which this sequence was generated from the parental strand, since a PCR cycle counter sequence generated earlier in the PCR amplification will have a larger number of copies than a PCR cycle counter sequence generated later in the PCR amplification. The PCR cycle counter also provides additional opportunities for error correction of the nucleic acid sequence reads, as discussed further below. The PCR cycle counter can alternatively be referred to as a "PCR cycle identifier", since it allows a skilled person to differentiate between amplicons generated in different PCR cycles, or a PCR cycle tracer or PCR cycle tracker.

For those oligonucleotides comprising both universal and non-universal bases in the first strand (for double stranded oligonucleotides) or in the only strand (for single stranded oligonucleotides), the universal bases in the oligonucleotide may be contiguous or non-contiguous. A non-contiguous arrangement of universal bases (where the universal bases such are interspersed with one or more non-universal bases) may be preferred to confer increased stability. In addition, the positions of the universal bases may be varied between oligonucleotides in a given pool to provide additional combinations of possible PCR cycle counter sequences for the daughter nucleic acid molecules produced in the PCR reaction.

The oligonucleotide may comprise a ligation moiety, for example at its 3' end for single stranded-adaptors or at the 3' end of the universal base-containing strand for double stranded oligos. Preferably, the oligonucleotide is a double stranded oligonucleotide having a ligation moiety at the 3' end of its universal base-containing strand and a ligation moiety at the 5' end of the second, complementary, strand. This allows both strands to be attached to the NAOI, and at both ends of the NAOI.

In one embodiment of the invention, the oligonucleotide is double-stranded and comprises two strands. The first strand comprises one or more universal nucleotide bases and has a ligation moiety at its 3' end. The second strand comprises a ligation moiety at its 5' end. The two strands hybridise together under stringent conditions. In another embodiment, the oligonucleotide is a single-stranded adaptor, wherein the oligonucleotide comprises one or more universal nucleotide bases and a ligation moiety at both ends. Such single-stranded adaptors would generally be hairpin oligos that have a cleavable moiety (for example a uracil nucleotide) to cleave the adaptor after ligation. Ultimately the functionality of such an oligonucleotide is the same as a double-stranded oligo.

Additional features of the oligonucleotide discussed herein apply equally to both the double and single-stranded embodiments, unless specified otherwise or dictated by the context.

The oligonucleotides may be DNA or RNA oligonucleotides, but are preferably DNA oligonucleotides.

In a preferred embodiment, the oligonucleotide is a double-stranded oligonucleotide, wherein the first strand is a PCR cycle counter generator that comprises one or more universal nucleotide bases and a ligation moiety at its 3' end, and wherein the second, complementary, strand comprises a ligation moiety at its 5' end. Complementary strands includes embodiments in which the oligonucleotides have non-complementary sections, for example in embodiments where the oligonucleotides are asymmetrical adaptors having a non-complementary section.

The second strand of double-stranded oligonucleotides will generally not comprise any universal bases. However, in some embodiments the second strand may also comprise universal bases.

"Ligation moiety" refers to any nucleotide sequence capable of ligation. Exemplary ligation moieties include overhangs and blunt ends. Overhangs may be an overhang of one or more bases. Single base overhangs are preferred, and a single T base overhang is most preferred. The overhangs can be universal or non-universal bases. The overhang is preferably a non-universal base overhang. Ligation moiety may also refer to a 5' phosphate group. If an oligonucleotide comprises an overhang, the oligonucleotide may optionally further comprise a phosphorothioate linkage between the universal base containing strand and the overhang. A phosphorothioate bond stops the adapter being digested by enzymes that have exonuclease activity The overall length of the oligonucleotide can vary depending on the design and the components that are incorporated into it. For example, the oligonucleotide may be at least 6, at least 8 or at least 10 nucleotides in length (or base pairs, in the case of a double-stranded oligonucleotide). In one embodiment, the oligonucleotide is from 6 to 100, from 6 to 75, from 10 to 75, from 15 to 75, or from 20 to 60 nucleotides in length (or base pairs, in the case of a double-stranded oligonucleotide). A length of 40 to 60 nucleotides or base pairs may be preferred. The precise length is not crucial and will depend on the features that are incorporated into the oligonucleotide.

In one embodiment, the arrangement of nucleotides in the first strand of a double-stranded oligonucleotide or in the only strand of a single-stranded oligonucleotide can be as follows, in a 5' to 3' order:

[asymmetric sequencing adaptor]-[PCR-cycle counter generator]-[filler]-[ligation moiety]

wherein:
the asymmetric sequencing adaptor comprises non-universal bases only, 5 to 50 bases in length;
the PCR cycle counter comprises a mixture of universal and non-universal base, 5 to 25 bases in length; and
the filler region comprises non-universal bases only, from 1 to 10 bases in length.

In one embodiment, the oligonucleotide is double-stranded, comprising two strands hybridised to each other. The first strand comprises at least 4 universal nucleotide bases and has a single non-universal base overhang as a ligation moiety at its 3' end. The second strand further comprises a ligation moiety at its 5' end. The oligonucleotide may be between 10 and 100 base pairs in length, optionally between 40 and 60 base pairs in length.

In one embodiment, the oligonucleotide comprises up to 100 complementary base pairs.

In use, a single arrangement of bases and ligation moieties might be used. For example, all oligonucleotides in a given pool or used in a given reaction might be identical. Alternatively, a mixture of two or more types of oligonucleotide (of different sequence) may be used to increase the diversity of PCR cycle counter sequences that are generated. For example, in one embodiment of the invention there is provided a mixture of oligonucleotides, wherein the mixture comprises at least 2 different oligonucleotides of the invention. The oligonucleotides differ in their sequence, for example such that the positions of the one or more universal bases are not identical in all oligonucleotides in the mixture, or alternatively the "constant" part of the oligonucleotide (consisting of non-universal bases) may differ between oligonucleotides to cause the relative positions of the universal bases to shift (hence providing more than one "type", i.e. sequence, of oligonucleotide). In such mixtures, the oligonucleotides may have two or more arrangements of universal and non-universal bases (i.e. sequences), but preferably the ligation moieties will not differ between oligonucleotides, i.e., each oligonucleotide will have a common ligation moiety. The mixtures may comprise more than 2 different types of oligonucleotides. For example, the mixture may comprise at least 2, at least 3, at least 4, at least 5, at least 6, at least 7, at least, 8, at least 9, or at least 10 different oligonucleotides. A mixture of at least 4 different oligonucleotides is preferred. In such mixtures, it is preferred that each oligonucleotide has at least 4 universal bases, where the arrangement (i.e., position) of universal and non-universal bases in each type of oligonucleotide in the mixture is different, and/or wherein the arrangement of non-universal bases differs to cause a shift in the relative locations of the universal bases. Preferably, in a mixture of different types of oligonucleotides, no one type of oligonucleotide has all its universal bases in the same position as another type of oligonucleotide in the mixture. However, certain nucleotide positions may have a universal base in the same place in more than one type of oligonucleotide, thus the position of a universal base may be fixed in the tag. For example, in a mixture of 4 different types of oligonucleotides A, B, C and D, each oligonucleotide having at least 4 universal bases, the positions of the universal bases within the PCR cycle counter generator portion of the oligonucleotide could be:

Oligonucleotide type A may have universal bases at the 3rd, 5th, 7th and 9th positions (counting from the 5' end of the PCR cycle counter generator portion of the oligonucleotide);
Oligonucleotide type B may have universal bases at the 2nd, 3rd, 6th, 8th and 9th positions;

Oligonucleotide type C may have universal bases at the 3rd, 7th, 10th and 12th positions; Oligonucleotide type D may have universal bases at the 4rd, 6th, 8th, 9th and 12th positions.

Another example of a mixture is as follows, where the arrangement of non-universal bases causes the relative positions of the universal bases within the PCR cycle counter generator portion of the oligonucleotide to shift with respect to the other members of the mixture:

Oligonucleotide type A may have universal bases at the 9th, 12th, 15th and 20th positions (counting from the 5' end of the PCR cycle counter generator portion of the oligonucleotide);

Oligonucleotide type B may have universal bases at the 10th, 13th, 16th and 21st positions;

Oligonucleotide type C may have universal bases at the 11th, 14th, 17th and 22nd positions;

Oligonucleotide type D may have universal bases at the 12th, 15th, 18th and 23rd positions.

Alternatively, the positions of the universal bases may be fixed and the sequence of the non-universal bases may change. In some embodiments, a combination of these two types of variations may be used. The context will determine the level of heterogeneity in PCR cycle counter sequence that is needed and hence the oligonucleotide or oligonucleotide pool complexity.

The precise design of the oligonucleotides is not fixed and the skilled person would understand how to create a mixture of different types of oligonucleotides that can provide a sufficient number of different PCR cycle counter sequences, as required by the context.

The number of possible PCR cycle counter sequences that can be generated using the oligonucleotides or mixtures of the invention can be at least 2, at least 3 or at least. Preferably, the oligonucleotide or mixture of oligonucleotides is capable of producing at least 4 different PCR cycle counter sequences.

The oligonucleotides, including the mixtures of oligonucleotides, may be provided in aqueous solution.

In some embodiments, the oligonucleotide that contains the universal base may also preferably contain a sequencing adaptor (or partial sequencing adaptor). This may be referred to as a one-step ligation method, since a single ligation can be used to attach both the oligonucleotide to generate the PCR cycle counter sequence on the NAOI and the sequencing adaptor to allow sequencing of the NAOI. In such an embodiment, the sequencing adaptors will be at the 5' end of the oligonucleotide for single stranded oligonucleotides, and for double-stranded oligonucleotides, the sequencing adaptor is at the 5' end of the universal-base containing strand, and the 3' end of the complementary strand. The sequencing adaptor may be partial Illumina adapter sequences, whereby the strand with the universal bases contains the partial P5 illumina adapter sequence and the complementary strand contains a partial P7 illumina adapter sequence. A vice versa arrangement is of course also possible (the strand with the universal bases contains the partial P7 illumina adapter sequence and the complementary strand contains a partial P5 illumina adapter sequence)

Sequencing adaptors may be asymmetric. Asymmetric adaptors generally comprise a complementary section and a non-complementary section. Sequencing adaptors may incorporate sequencing primer sites and/or universal primer sites into the NAOI.

The oligonucleotides may be provided as a pool of oligonucleotides. The pool of oligonucleotides may comprise at least 4 different types of oligonucleotide of the invention. In some embodiments, all of the oligonucleotides may be of the same length (or differing in length by only up to 3 nucleotides) but differ according to the arrangement of universal and/or non-universal bases. The pool may comprise at least 1000 oligonucleotides of the invention.

The oligonucleotides have a known sequence as they are artificially produced. Hence, although the PCR cycle counter sequences are degenerate and produced at random, the oligonucleotides are not degenerate since the sequence of each is known Further possible components of the oligonucleotides include an index sequence. Alternatively, index sequences may be separately attached to the NAOI. The index sequence can be used to identify the sample in subsequent sequencing and analysis. Therefore, the index sequence may be unique to the sample from which the NAOIs are derived (or the sample in which the NAOIs are present). An index sequence may also be used when sample replicates are used to identify which replicate the sequence originates from.

In some embodiments, the oligonucleotide comprises a filler region. The filler region may be adjacent to the PCR cycle counter generator. The filler region may be a stretch of nucleotides between 1 and 20 nucleotides in length. In some embodiments, the filler region is a stretch of nucleotides from 1 to 20, or from 1 to 15, or from 1 to 10 or from 1 to 5 nucleotides in length.

For a given pool of oligonucleotides, the filler region may be the same in each of the oligonucleotides in the pool. However, when the oligonucleotides are double stranded, the filler region may be the same in each of the oligonucleotides in the pool with the exception of the filler region of one strand in each oligonucleotide in the pool being one or more nucleotides longer. In other words, the filler region may comprise an overhang. The overhang may act as a ligation moiety to allow attachment of the oligonucleotides to the NAOIs.

Each oligonucleotide may comprise a universal priming site, or may incorporate universal priming sites into the NAOIs. When the oligonucleotides in the pool are double stranded, each strand of each oligonucleotide may comprise a universal priming site, or may incorporate universal priming sites into the both strand of the NAOIs. The universal priming sites are used to amplify the labelled NAOI, for example by using PCR.

In embodiments where the oligonucleotide comprises a one or more priming sites, the oligonucleotide may comprise an N nucleotide (A, T, G or C, or other non-universal base) immediately adjacent to the priming sites. This N nucleotide acts to interrupt long stretches of complementarity in DNA molecules that have the same or similar variable length oligonucleotides ligated to each end, since long stretches of uninterrupted complementarity can result in DNA secondary structure formation and in complications during sequencing. This N nucleotide will differ between oligonucleotides in the same pool (i.e. the pool of oligos will have a mixture of different nucleotides at this position)

Accordingly, each oligonucleotide may comprise, in order, a sequencing adaptor, a PCR cycle counter generator sequence, a filler region, and a ligation moiety. The filler region may also act as a ligation moiety (for example when the filler region comprises an overhang). When the oligonucleotide is a double stranded oligonucleotide, the first strand may comprise, in a 5' to 3' order, a sequencing adaptor, a PCR cycle counter generator sequence, a filler region, and a ligation moiety, and the second (complementary) strand may comprise in a 3' to 5' order, a sequencing adaptor, a region complementary to the PCR counter generator sequence, a filler region, and a ligation moiety. The oligonucleotide may comprise a non-complementary region, in the case of asymmetric oligonucleotides. The non-complementary region allows differential labelling of the two strands of the oligonucleotide (and hence of the two strands of the NAOI to which the oligonucleotide is attached). References to sequencing adaptors herein include partial sequencing adaptors, i.e. adaptors suitable for use in a next generation sequencing system. Note the asymmetric or sequencing adaptors (partial or otherwise) may contain the sequencing and/or universal priming site(s). In other words, the sequencing adaptors, if present, may act as first and second priming sites for the subsequent PCR reaction and/or sequencing steps. Incorporation of sequencing adaptors into the NAOIs in this way is known to the skilled person.

In one embodiment, the oligonucleotide comprises a PCR cycle counter generator sequence and a sequencing adaptor. In one embodiment, the oligonucleotide comprises a PCR cycle counter generator sequence, a sequencing adaptor and a filler sequence. In one embodiment, the oligonucleotide comprises a PCR cycle counter generator sequence, a sequencing adaptor, a filler sequence, and a molecular barcode.

Double stranded oligos used in the invention may comprise an asymmetrical portion, for example an asymmetric sequencing adaptor.

The order of the components is not absolutely fixed, but the following double-stranded oligonucleotides having a first and second strand may be used in the methods of the invention:
  a) a first strand comprising, in a 5' to 3' order, a sequencing adaptor, a PCR cycle counter generator sequence and a ligation moiety, and a second strand comprising, in a 3' to 5' order, a sequencing adaptor, a region complementary to the PCR cycle counter generator sequence, and a ligation moiety;
  b) a first strand comprising, in a 5' to 3' order, a sequencing adaptor, a PCR cycle counter generator sequence, a filler region, and a ligation moiety, and a second strand comprising, in a 3' to 5' order, a sequencing adaptor, a region complementary to the PCR cycle counter generator sequence, a complementary filler region, and a ligation moiety;
  c) a first strand comprising, in a 5' to 3' order, a sequencing adaptor, a molecular barcode, a PCR cycle counter generator sequence, a filler region, and a ligation moiety, and a second strand comprising, in a 3' to 5' order, a sequencing adaptor, a complementary molecular barcode, a region complementary to the PCR cycle counter generator sequence, a complementary filler region, and a ligation moiety;
  d) a first strand comprising, in a 5' to 3' order, a sequencing adaptor, a PCR cycle counter generator sequence, a molecular barcode, a filler region, and a ligation moiety, and a second strand comprising, in a 3' to 5' order, a sequencing adaptor, a region complementary to the PCR cycle counter generator sequence, a complementary molecular barcode, a complementary filler region, and a ligation moiety;
  e) a first strand comprising, in a 5' to 3' order, a sequencing adaptor, a first primer binding site, a PCR cycle counter generator sequence, a filler region, and a ligation moiety, and a second strand comprising, in a 3' to 5' order, a sequencing adaptor, a second primer binding site complementary to the first primer binding site, a region complementary to the PCR cycle counter generator sequence, a complementary filler region, and a ligation moiety; or
  f) a first strand comprising, in a 5' to 3' order, a sequencing adaptor, a first primer binding site, a molecular barcode, a PCR cycle counter generator sequence, a filler region, and a ligation moiety, and a second strand comprising, in a 3' to 5' order, a sequencing adaptor, a second primer binding site complementary to the first universal priming site, a complementary molecular barcode, a region complementary to the PCR cycle counter generator sequence, a complementary filler region, and a ligation moiety; or
  g) a first strand comprising, in a 5' to 3' order, a sequencing adaptor, a first primer binding site, a PCR cycle counter generator sequence, a molecular barcode, a filler region, and a ligation moiety, and a second strand comprising, in a 3' to 5' order, a sequencing adaptor, a second primer binding site complementary to the first universal priming site, a region complementary to the PCR cycle counter generator sequence, a complementary molecular barcode, a complementary filler region, and a ligation moiety.

Note the first and second primer sites are generally complementary to each other. In addition, the first and second primer binding sites may be contained within the sequencing adaptors. Such sequencing adaptors would generally comprise an asymmetric portion, and a complementary portion. The first and second primer binding sites may be contained within the complementary portion containing, or the first and second primer binding sites may span the complementary and non-complementary sections. The primer sites may be used in the subsequent PCR reaction and/or sequencing steps. The benefit of including the sequencing adaptors in the oligos is that it avoids the need for a further ligation step to attach the sequencing adaptors to the NAOIs.

In addition to the above arrangements, in particular when the oligo does not already contain asymmetrical sequencing adaptors, the oligo may further comprise a ligation moiety at the 5' end of the universal base-contain strand to allow ligation of sequencing adaptors. In any of the above arrangements, the oligo may further comprise a ligation block at the 3' end of the complementary strand to prevent blunt-ended ligation to a second adapter (adapter dimerization).

The region complementary to the PCR cycle counter generator sequence will usually not comprise any universal bases.

In one embodiment of the invention, the oligonucleotide does not comprise any ligation blocks. "Ligation block" refers to any sequence or moiety that prevents ligation of the nucleic acid to another nucleic acid or nucleotide base. Any suitable ligation block can be used, for example a non-phosphorylated nucleotide, an inverted dT, a C3 spacer, or a 3' phosphate group. A non-phosphorylated nucleotide is preferred.

Attachment of the Oligonucleotides

The oligonucleotides are attached to the NAOIs at either or both ends (or, in the case of multiple NAOIs, a mixture thereof, i.e. some NAOIs will have oligonucleotides attached at one end, some NAOIs will have oligonucleotides attached at both ends). Attachment may be achieved by any suitable method, for example ligation, PCR, polymerase extension, isothermal/rolling circle amplification, loop-mediated isothermal amplification, or strand-displacement amplification. Ligation of the oligonucleotides may be preferred.

Ligation reactions can be carried out according to any suitable method known to the skilled person, although generally ligation enzymes (ligases) will be used. The ligase may be a DNA or RNA ligase. In some embodiments, the ligase is a T4 DNA ligase.

To promote ligation of the NAOI to the oligonucleotide, the nucleic acid of interest may comprise a ligation moiety at the end of one or each of the strands of the nucleic acid of interest (or such moieties may be added). The ligation moiety may be an overhang that is complementary to the 3' ligation moiety on the oligonucleotide to enable association and ligation of the two molecules together. If no such ligation moiety is present on the NAOI, then the method may further comprise the step of adding a ligation moiety to the end of one or each of the strands of the nucleic acid of interest. Depending on the nature of the ligation moiety, it may be present (or added) to the 3' end of one or each of the strands of the NAOI. For example, a single base overhang at the 3' end of a strand of a NAOI will promote ligation of the 3' end of a double stranded oligonucleotide to the 5' end of the complementary strand of the double stranded NAOI. (Of course, double stranded oligonucleotides of the present invention are not fully complementary given the presence of universal bases, but they are sufficiently complementary to allow hybridisation, in particular they are complementary with respect to all non-universal bases, with the exception of any overhangs). Ligation moieties used on the NAOI may preferably overhangs, more preferably a G or A overhang, and further preferably a single A base overhang (but the use of such a specific ligation moiety is not essential). Generally, the ligation moiety is not a universal base.

The NAOI may be processed in other ways prior to attachment of the oligonucleotide. For example, the NAOI may have undergone fragmentation and/or end repair. In some embodiments of the invention, the methods may include a step of fragmenting the NAOI and/or end repair of the NAOI. The NAOI may also be phosphorylated at the 5' end(s) and/or have an A-tail added at the 3' end(s).

In some embodiments, depending on the method used, the step of end-repairing the NAOI may also provide a suitable A-tail (for example when using a polymerase to end-repair the NAOI). Other processing steps include amplification of the NAOI, for example using whole genome amplification, to increase the overall amount of the NAOI in the reaction before attaching the oligonucleotides.

Purification and Enrichment Steps

In some embodiments, the methods of the invention may also comprise purification of the reaction mixture, e.g., to remove un-ligated oligonucleotides (and/or un-ligated asymmetric adaptors). This can be achieved according to any suitable method known to the skilled person. For example, purification may comprise the use of magnetic SPRI beads. Such beads are paramagnetic (magnetic only in a magnetic field) and this prevents them from clumping and falling out of solution. Each bead is made of polystyrene surrounded by a layer of magnetite, which is coated with carboxyl molecules. These reversibly bind DNA in the presence of a crowding agent (for example polyethylene glycol (PEG) and salt (20% PEG, 2.5M NaCl)). PEG causes the negatively-charged DNA to bind with the carboxyl groups on the bead surface. As the immobilization is dependent on the concentration of PEG and salt in the reaction, the volumetric ratio of beads to DNA is critical. Magnetic SPRI beads can be used for size separation, for example to distinguish between tagged NAOI and shorter, un-ligated oligonucleotides that remain in the reaction mixture. DNA fragment size affects the total charge per molecule with larger DNAs having greater charges; this promotes their electrostatic interaction with the beads and displaces smaller DNA fragments. The size of fragments eluted from the beads (or that bind in the first place) is therefore determined by the concentration of PEG, and this in turn is determined by the mix of DNA and beads. A 50ul DNA sample plus 50ul of beads will give a SPRI:DNA ratio of 1. As this ratio is changed the length of fragments binding and/or left in solution also changes. The lower the ratio of SPRI:DNA the longer the final fragments will be at elution. Smaller fragments (i.e., the un-ligated oligonucleotides) retained in the buffer can be discarded. The precise method used for a given reaction mixture can be determined by the skilled person who will be familiar with such purification methods.

Other methods of purification, e.g., for removing un-ligated oligonucleotides, include the use of a single-strand nuclease to digest any un-ligated oligonucleotides. Such a method is generally only suitable when single-stranded oligonucleotides are being used.

Combination with Molecular Barcoding and Other Techniques for Enhancing Sensitivity Importantly, the methods of the invention can be combined with molecular barcoding techniques. The methods of the invention provide additional sensitivity to "traditional" molecular barcoding techniques, since the PCR cycle counter gives an indication of when a molecule was generated during the amplification process. Similarly, although identification of individual starting molecules is not necessary when performing the PCR cycle counter methods of the invention, the ability to identify individual starting molecules adds further sensitivity when calling mutations or variations in the NAOI sequence. In this way, the PCR cycle counter generator and molecular barcoding methods can work synergistically to provide a highly sensitive method for detecting low allelic fraction mutations in nucleic acids.

In one embodiment, the invention provides a method of sequencing nucleic acids of interest (NAOIs), comprising:
 a. providing a sample comprising parental NAOIs;
 b. attaching oligonucleotides to the parental NAOIs to provide labelled parental NAOIs, wherein the oligonucleotides comprise a PCR cycle counter generator sequence comprising at least one universal nucleotide base and a molecular barcode;
 c. amplifying the tagged and labelled parental NAOIs using PCR to provide an amplified library of daughter NAOIs each containing a PCR cycle counter sequence and a barcode sequence;
 d. sequencing the amplified library of daughter NAOIs to provide a set of sequence reads, wherein each sequence read comprises a NAOI-originating component, a PCR cycle counter component and a barcode component; and
 e. distinguishing true variants in parental NAOI sequences from false variants in parental NAOI sequences.

Alternatively, a separate step of tagging the parental NAOIs with a molecular barcode may happen before or after the oligonucleotide comprising the PCR cycle counter generator is attached to the NAOI. In some embodiments, the oligonucleotide itself may comprise a unique molecular identifier (UMI), such as a barcode. In this way, the PCR cycle counter generator sequence and the UMI may be attached to the NAOI in a single reaction. UMIs are also referred to in the art as unique identifiers (UIDs), single molecule identifiers (SMIs) and molecular barcodes.

In methods comprising sequential steps of adding the PCR cycle counter generator and the UMI (in either order), the skilled person will be aware that certain washing or other purification steps may be necessary between attaching the components to try and ensure the NAOIs have both a PCR cycle counter generator and a UMI attached, and to minimise competition or interactions between the oligonucleotide and the UMI.

In sequential methods, the step of adding the first component may also comprise adding a further ligation moiety to allow the second component to be attached.

It is specifically contemplated than any method of uniquely labelling the starting (parental) NAOIs can be used in combination with the PCR cycle counter methods of the invention. When methods of the invention allow individual starting molecules to be identified, errors in the sequence reads can be identified more readily.

Example methods of uniquely labelling nucleic acids prior to PCR and other methods to improve accuracy NGS and PCR based methods include those described in US2012/0071331, WO2013/142389, US2014/0227705 and US2016/0222378.

US2012/0071331 describes methods and compositions for determining the number of individual polynucleotide molecules originating from the same genomic region of the same original sample that have been sequenced in a particular sequence analysis configuration or process. A degenerate base region (DBR) is attached to the starting polynucleotide molecules that are subsequently sequenced (e.g., after certain process steps are performed, e.g., amplification and/or enrichment). The number of different DBR sequences present in a sequencing run can be used to determine/estimate the number of different starting polynucleotides that have been sequenced. DBRs can be used to enhance numerous different nucleic acid sequence analysis applications, including allowing higher confidence allele call determinations in genotyping applications. Such methods may comprise attaching an adapter to NAOIs in multiple different samples, where the adapter for each sample includes: a unique MID specific for the sample; and a degenerate base region (DBR) (e.g., a DBR with at least one nucleotide base selected from: R, Y, S, W, K, M, B, D, H, V, N, and modified versions thereof); pooling the multiple different adapter-attached samples to generate a pooled sample; incorporating a PCR cycle counter generator sequence as described herein (either before or after pooling); amplifying the adapter-attached NAOIs in the pooled sample; sequencing a plurality of the amplified adapter-attached NAOIs, where the sequence of the MID, the DBR, the PCR cycle counter generator and at least a portion of the NAOIs is obtained for each of the plurality of adapter-attached polynucleotides; and (5) determining the number of distinct DBR sequences present in the plurality of sequenced adapter-attached NAOIs from each sample to determine or estimate the number of starting NAOIs from each sample that were sequenced in the sequencing step.

WO2013/142389 describes a method of Duplex Consensus Sequencing (DCS). This approach greatly reduces errors by independently tagging and sequencing each of the two strands of a NAOI duplex. As the two strands are complementary, true mutations are found at the same position in both strands. The methods use a single molecule identifier (SMI) adaptor molecule for use in sequencing a double-stranded target NAOI molecule. Said SMI adaptor molecule includes a single molecule identifier (SMI) sequence which comprises a degenerate or semi-degenerate DNA sequence; and an SMI ligation adaptor that allows the SMI adaptor molecule to be ligated to the double-stranded target NAOI sequence. The SMI sequence may be single-stranded or double-stranded. A method incorporating the use of the SMI may comprise ligating a double-stranded target NAOI to at least one SMI adaptor molecule to form a double-stranded SMI-target nucleic acid complex, either before or after incorporation of the PCR cycle counter generator; amplifying the double-stranded SMI-NAOI complex, resulting in a set of amplified SMI-target NAOI products; and sequencing the amplified SMI-target NAOI products.

In some embodiments, the NAOIs (or the sample comprising the NAOIs) is contacted with a molecular barcode library. Molecular barcodes from the library are attached to the NAOIs prior to amplification by PCR.

Kits for molecular barcoding are available, for example HaloPlex$^{HS}$ (Agilent), SureSelect XT HS (Agilent), Thruplex Tag-Seq (Rubicon) and MBC Adapters (ArcherDX).

Further example methods for molecular barcoding are discussed in, for example, Stahlberg et al., 2016, *Nucleic Acids Res.*, 44(11):e105, Shokralla et al., 2014, *Mol Ecol Resour*, 14(5):892-901 and Cruaud et al., 2017, 7:41948.

However, it is not always necessary to include a molecular barcode to uniquely identity starting molecules. Although synthetic identifiers such as molecular barcodes are useful, natural molecular identifiers, such as the natural breakpoints in the NAOIs, may also allow the original NAOI to be identified or inferred.

When the PCR cycle counter methods of the invention are combined with a method that allows the starting NAOIs to be uniquely identified, for example when combining the method with molecular barcoding, it is possible to generate a consensus sequence for the NAOI. This is discussed further below.

Additional Optional Steps Prior to Sequencing

After attachment of the oligonucleotide(s) to the NAOI, the resulting labelled NAOI may undergo further processing, either before or after amplification. For example, a further ligation moiety may be added to the 3' end of one or each of the strands of the NAOI. A polymerase used in the amplification step may incorporate such a ligation moiety itself. For example, Taq DNA polymerase may generate a single A base overhang at the 3' end of the extended strand(s) of the NAOI.

After attaching the oligonucleotide, methods of the invention may further comprise a step of adding further components to the NAOI, for example adding molecular barcode (as discussed above) and/or by differentially labelling the strands of the labelled NAOI. This latter step enables the two strands to be distinguished from one another following subsequent PCR amplification and sequencing.

Differential labelling of the strands of the labelled NAOI can be achieved according to any method known to a skilled person, although generally this will be achieved using asymmetric adaptors, such as Y-stem adaptors. Asymmetric adaptors are double-stranded adaptors having a complementary section and a non-complementary section. The complementary section is a section where the two sequences are complementary and hybridised together. This end of the asymmetric adaptor is ligated to the labelled NAOI. The non-complementary section of the asymmetric adaptor acts as the label for the two strands. The different sequences of the two strands in the non-complementary section of the asymmetric adaptor allow the incorporation of a different label on each of the two strands of the tagged NAOI. Suitable Y-stem adaptors include P7/P5 adaptors (Illumina), although the present invention is not limited to the use of these specific adaptors. Preferably, asymmetric labelling of the tagged double-stranded NAOI occurs at each end of the tagged double-stranded NAOI molecule. Preferably the asymmetric adaptors are part of the oligonucleotide containing the PCR cycle counter, to avoid the need for a separate ligation step.

The asymmetric adaptors may comprise an index sequence. The index sequence can be used to identify the sample in subsequent sequencing and analysis. Alternatively, an index sequence may be incorporated at an alternative step in the method (for example the oligonucleotides comprising the PCR cycle counter generator may also comprise an index sequence that is unique to the sample being analysed).

In a preferred embodiment, the oligonucleotides comprising the PCR cycle counter also comprise a sequencing adaptor having a non-complementary section and a complementary section and a molecular barcode.

Amplification of the Labelled (and Optionally Tagged) NAOI

After the NAOIs have been labelled (using the oligonucleotides) and optionally tagged (for example using a molecular barcode, preferably using the same oligonucleotide that comprises the PCR cycle counter), the NAOIs may be amplified, for example using PCR, to enable further processing and analysis.

In one embodiment of the invention, the method comprises
  a. providing a sample comprising parental NAOIs;
  b. attaching oligonucleotides to the parental NAOIs to provide labelled parental NAOIs, wherein the oligonucleotides comprise a PCR cycle counter generator sequence comprising at least one universal nucleotide base;
  c. amplifying the labelled parental NAOIs using PCR to provide an amplified library of daughter NAOIs each containing a PCR cycle counter sequence;
  d. sequencing the amplified library of daughter NAOIs to provide a set of sequence reads, wherein each sequence read comprises a NAOI-originating component and a PCR cycle counter component; and
  e. distinguishing true variants in parental NAOI sequences from false variants in parental NAOI sequences.

The method may comprise additional amplification steps. For example, in one embodiment, the method may comprise an additional PCR amplification step that incorporates sequencing adaptors into the NAOIs after incorporation of the PCR cycle counter generator and in situ PCR cycle counter sequence generation and prior to sequencing.

Amplification is generally conducted using PCR. In preferred methods of the invention, NAOI are labelled with oligonucleotides of the invention that incorporate primer binding sites. When the NAOI has been labelled with the oligonucleotides, the PCR uses primers directed against the primer binding sites. Such primers may comprise a sample identifier (for example an index sequence) to enable the sample to be identified during subsequent analysis.

In one embodiment of the invention, the NAOI is double stranded and comprises a first strand and a second strand. The 5' ends of the first and seconds strand of the NAOI are attached to 3' ends of the universal-base containing strands of two oligonucleotides of the inventions. The 3' ends of the first and second strands of the NAOI are attached to the 5' ends of the non-universal base containing strands of the two oligonucleotides of the invention.

When the oligonucleotides of the invention incorporate universal binding sites into the NAOIs, the first universal binding site is positioned upstream (i.e. 5') of the PCR cycle counter generator (and the second universal binding site is positioned downstream (i.e. 3') of the sequence complementary to the PCR cycle counter generator). This allows the PCR cycle counter sequence to be generated in the subsequent amplification reaction.

In some embodiments, the methods of the invention may comprise a step of target enrichment. The target enrichment step, if present, is generally conducted after the NAOI is labelled with the oligonucleotide (and optionally with the asymmetric labels). In some embodiments, target enrichments is conducted after the labelled NAOI has been amplified in the first PCR reaction. Target enrichment can be carried out according to any method known to the skilled person, for example as discussed in Mamanova et al., "Target-enrichment strategies for next-generation sequencing", 2010, *Nature Methods*, 7:111-118 or Bodi et al., "Comparison of Commercially Available Target Enrichment Methods for Next-Generation Sequencing", 2013, J Biomol Tech., 24(2):73-86, each of which are incorporated herein by reference. Target enrichment allows the subsequent sequencing and analysis steps to focus on a genetic region of interest. Methods of target enrichment include RNA probe enrichment (for example Agilent™ SureSelect™ target enrichment), DNA probe enrichment (for example NimbleGen™ SeqCap EZ Choice™ enrichment) or array-based enrichment (for example NimbleGen™ array capture enrichment). Enrichment when used in the methods of the invention is a separate step of the method and does not occur as part of the ligation and extension reactions.

The methods of the invention may comprise a number of amplification reactions. For example, and most commonly, amplification of the NAOIs may be carried out after the NAOIs are labelled with the PCR cycle counter generator. In addition, amplification may be carried out prior to tagging to increase the amount of starting molecules. If target enrichment is conducted, a subsequent amplification may also be employed in the method. Clonal amplification can be undertaken as part of the step of determining the sequence of the NAOI.

When amplification steps comprising PCR are conducted after the PCR cycle counter generator sequence has been added to the NAOI, a new PCR cycle counter sequence is created for each labelled molecule that is copied in each cycle of the PCR.

In one embodiment of the invention, the method comprises:
  a) providing a sample comprising NAOIs;
  b) optionally end repairing, 5' phosphorylating and/or 3' A-tailing the NAOIs;
  c) ligating an oligonucleotide of the invention to the NAOIs, wherein the oligonucleotides incorporate a universal priming sites and a PCR cycle counter generator into the NAOI;
  d) conducting PCR using primers directed against the universal priming sites to amplify NAOIs with oligonucleotides attached;
  e) enriching the sample using target-based enrichment, for example in-solution hybridisation;
  f) performing a further PCR amplification on the enriched product
  g) sequencing the PCR reaction product (i.e. the NAOIs).

In one embodiment of the invention, the method comprises:
  a) providing a sample comprising NAOIs;
  b) optionally end repairing, 5' phosphorylating and/or 3' A-tailing the NAOIs;

c) ligating an oligonucleotide of the invention to the NAOIs, wherein the oligonucleotides incorporate sequencing adaptors and a PCR cycle counter generator into the NAOI;
d) conducting PCR amplify NAOIs with oligonucleotides attached;
e) enriching the sample using target-based enrichment, for example in-solution hybridisation;
f) performing a further PCR amplification on the enriched product
g) sequencing the PCR reaction product (i.e. the NAOIs).

In one embodiment of the invention, the method comprises:
a) providing a sample comprising NAOIs;
b) optionally end repairing, 5' phosphorylating and/or 3' A-tailing the NAOIs;
c) ligating an oligonucleotide of the invention to the NAOIs, wherein the oligonucleotides incorporate a molecular barcode, universal priming sites and a PCR cycle counter generator into the NAOI;
d) conducting PCR using primers directed against the universal priming sites to amplify NAOIs with oligonucleotides attached;
e) enriching the sample using target-based enrichment, for example in-solution hybridisation;
f) performing a further PCR amplification on the enriched product
g) sequencing the PCR reaction product (i.e. the NAOIs).

In one embodiment of the invention, the method comprises:
a) providing a sample comprising NAOIs;
b) optionally end repairing, 5' phosphorylating and/or 3' A-tailing the NAOIs;
c) ligating an oligonucleotide of the invention to the NAOIs, wherein the oligonucleotides incorporate a molecular barcode, sequencing adaptors and a PCR cycle counter generator into the NAOI;
d) conducting PCR to amplify NAOIs with oligonucleotides attached;
e) enriching the sample using target-based enrichment, for example in-solution hybridisation;
f) performing a further PCR amplification on the enriched product
g) sequencing the PCR reaction product (i.e. the NAOIs).

In one embodiment of the invention, the method comprises:
a) providing a sample comprising NAOIs;
b) optionally end repairing, 5' phosphorylating and/or 3' A-tailing the NAOIs;
c) ligating an oligonucleotide of the invention to the NAOIs, wherein the oligonucleotides incorporate a universal priming sites and a PCR cycle counter generator into the NAOI;
d) purifying of the reaction mixture to remove un-ligated oligonucleotides;
e) conducting PCR using primers directed against the universal priming sites to amplify NAOIs with oligonucleotides attached;
f) purifying of the reaction mixture to remove universal primers;
g) optionally quantifying the PCR reaction product;
h) enriching the sample using target-based enrichment, for example in-solution hybridisation;
i) performing a further PCR amplification on the enriched product
j) optionally quantifying the PCR reaction product; and
k) sequencing the PCR reaction product (i.e. the NAOIs).

In one embodiment of the invention, the method comprises:
a) providing a sample comprising NAOIs;
b) optionally end repairing, 5' phosphorylating and/or 3' A-tailing the NAOIs;
c) ligating an oligonucleotide of the invention to the NAOIs, wherein the oligonucleotides incorporate a universal priming sites and a PCR cycle counter generator into the NAOI;
d) purifying of the reaction mixture to remove un-ligated oligonucleotides;
e) conducting PCR using primers directed against the universal priming sites to amplify NAOIs with oligonucleotides attached;
f) purifying of the reaction mixture to remove universal primers;
g) optionally quantifying the PCR reaction product;
h) enriching the sample using target-based enrichment, for example in-solution hybridisation is performed;
i) performing a further PCR amplification on the enriched product
j) optionally quantifying the PCR reaction product; and
k) sequencing the PCR reaction product (i.e. the NAOIs).

Sequencing the Amplified NAOIs

Determining the sequence of the labelled, amplified and optionally enriched NAOI can be carried out according to any suitable method known to the skilled person. However, given the number of NAOIs that will be analysed in any given method, next-generation sequencing (NGS) methods are preferred. Next-generation sequencing is also referred to as high-throughput sequencing and massively-parallel sequencing in the art, and is known and understood by the skilled person. A review of next-generation sequencing techniques is provided in Goodwin et al., "Coming of age: ten years of next-generation sequence technologies", 2016, *Nature Reviews*, 17:333-351.

The next-generation sequencing employed by the present invention may be selected from the group consisting of sequence-by-synthesis (SBS), sequencing-by-ligation (SBL) and long-read sequencing (LRS). The sequencing-by-synthesis may be selected from the group consisting of cyclic reversible termination SBS and single-nucleotide addition SBS. The long-read sequencing may be selected from the group consisting of single-molecule LRS and synthetic long-read LRS. Methods of sequence determination using sequencing-by-synthesis may be preferred.

Accordingly, in some embodiments of the invention, the method may further comprise localising tagged nucleic acids of interest to discrete sites. The discrete sites may comprise a solid or semi-solid substrate. The method may also comprise hybridizing or immobilising the tagged nucleic acids of interest to the solid or semi-solid substrate and clonally amplifying the localised and tagged NAOIs.

Sequencing the labelled and amplified NAOIs provides a library or set of sequence reads. Each sequence read comprises a NAOI-originating component and a PCR cycle counter component. The sequence reads will also comprise sequences derived from other components that have been attached to the NAOIs, either as part of the oligonucleotide or in a separate reaction step.

For example, in one embodiment, the sequence reads comprise a NAOI-originating component, a PCR cycle counter component, and a molecular barcode. The molecular barcode allows individual starting molecules to be identified.

Error Correction and Sequence Read Analysis Methods

Methods of the present invention comprise analysing the sequence reads to determine the presence or absence of genetic alterations in the NAOI. The methods therefore comprise distinguishing or inferring true variants in NAOI sequences from false variants in NAOI sequences.

The present invention is therefore useful in identifying true genetic alterations (for example mutations) in a NAOI and distinguishing such alterations from "false" alterations introduced by the steps of the method, in particular during PCR and sequencing. The polymerases used in PCR are not 100% accurate. Indeed, when using a Taq polymerase, the error rate may be 0.01%. However, the present invention is useful in identifying these errors. The present invention is therefore also useful in determining the true sequence of a NAOI, such as determining the presence or absence of variations in a NAOI (such as a SNP).

There are many suitable methods for distinguishing true variants in NAOI sequences from false variants in NAOI sequences and, given the content of the present disclosure, suitable methods would be apparent to the skilled person, given the information the PCR cycle counter generator provides in the resulting sequence read library.

In some embodiments of the invention, distinguishing true variants in parental NAOI sequences from false variants in a parental NAOI sequence comprises counting or quantifying the number of different PCR counter sequences. In particular, the method may comprise counting the number of different PCR cycle counter sequences originating from each parental NAOI or associated with each NAOI sequence in the sequence reads. Due to the nature of the present methods, the larger the number of different PCR counter sequences associated with each different NAOI-originating component or portion thereof, the higher probability there is of the variant being a true variant. The larger the number of different PCR counter sequences associated with each different NAOI-originating portion, the higher the probability the nucleic acid sequence accurately represents the parental NAOI.

In some embodiment, the methods comprise distinguishing sequence reads from each other according to the stage at which the sequence was made during the first PCR amplification reaction.

In some embodiments, the step of distinguishing true variants in parental NAOI sequence from false variants in parental NAOI sequence comprises quantifying the relative amount of each different PCR cycle counter for a given NAOI sequence. A gradual (e.g. logarithmic) decrease in the relative amount of each PCR cycle counter for a given NAOI sequence indicates the reads may have originated from the same starting molecule. For a given NAOI sequence, if there are multiple different PCR cycle counter sequences present in the same or similar quantity, they are likely to have originated from different starting molecules. If the same variant occurs in multiple starting molecules, the higher the probability the variant is a true call of the parental NAOI sequence.

When conducting PCR, the number of cycles of PCR is known, since the cycles are controlled according to the reaction conditions. Accordingly, in one embodiment of the invention, the step of distinguishing true variants in parental NAOI sequence from false variants in parental NAOI sequence comprises comparing the number of PCR cycle counter sequence associated with each different NAOI-originating portion with the number of PCR cycles performed in the PCR step that generated the PCR cycle counter sequences. When the number of different PCR counter sequences associated with a given NAOI-originating portion is greater than the number of PCR cycles performed, this is indicative of a true variant.

In one embodiment of the invention, the step of distinguishing true variants in a parental NAOI sequence from false variants in a parental NAOI sequence comprises:

a) grouping the sequence reads according to the sequence of the molecular barcode and optionally the sequence of the NAOI-originating component to group together all sequence reads arising from the same parental NAOI molecule;

b) counting the number of different PCR cycle counters associated each different NAOI-originating component sequences.

The NAOI-originating portion sequence having the highest number of different PCR cycle counters associated with it may be identified as the true parental NAOI sequence.

When the methods of the invention are combined with methods that allow the originating NAOI molecule to be identified, further methods of distinguishing or inferring true variants in NAOI sequences from false variants in NAOI sequences are made available.

For example, in one embodiment, the step of distinguishing or inferring true variants in NAOI sequences from false variants in NAOI sequences comprises a) grouping the sequence reads according to the sequence of the unique label or molecular barcode and optionally the sequence of the NAOI-originating component to group together all sequence reads arising from the same parental NAOI;

b) aligning the sequence reads according to the sequence of the NAOI-originating portion; and c) determining a consensus sequence for the parental NAOI The consensus sequence may represent the sequence with the highest probability of being the true sequence of the parental NAOI. The step of determining a consensus sequence may comprise identifying any nucleotide in the NAOI-originating portion of a sequence read for which more than one type of nucleotide is reported in a group of aligned sequence reads and counting the number of different PCR cycle counters associated with each reported nucleotide.

The nucleotide that is associated with the largest number of different PCR cycle counters may be selected for the consensus sequence. By selecting the nucleotide that is associated with the largest number of different PCR cycle counters, the method allows for error correction of the sequence reads. Specifically, the method allows for the correction of errors introduced during PCR or during sequencing.

In some embodiments, a consensus sequence comprises reads having common molecular barcode sequences being grouped together, and then collapsed to generate a consensus read. Sequencing positions may be discounted if the consensus group covering that position consist of fewer than 3 members, or if fewer than 90% of the sequences at that position in the consensus group had the identical sequence.

In one embodiment, the invention provides a method of error correcting nucleic acid sequence reads, the method comprising:

a. providing a dataset comprising a plurality of sequence reads from a sample, each sequence read comprising a NAOI-originating component and a PCR cycle counter component, and optionally a barcode component;

b. grouping sequence reads by the sequence of the PCR cycle counter, the NAOI-originating component and/or the barcode component; and c. correcting errors in the sequence reads, if necessary, to provide a consensus (true) sequence for each originating nucleic acid of interest.

The step of distinguishing/determining/inferred true variants in parental NAOI sequences from false variants in parental NAOI sequences may comprise the same steps.

In one embodiment of the invention, sequences are grouped by the sequence of the NAOI component of the sequence read and the sequence of the PCR cycle counter. The grouping can be done in either order. For example, the sequence reads may be grouped by the sequence of the NAOI-originating component and then sub-grouped according to the PCR cycle counter component, or the sequence reads may be grouped by the sequence of the PCR cycle counter component and then sub-grouped according to the NAOI-originating component—the ultimate effect is the same.

When the sequences of the NAOIs are compared between subgroups, different nucleotide may be reported at equivalent positions in different NAOIs sequences. It is then possible to select the NAOI sequence (or nucleotide at that position) having the highest number of different PCR cycle counter sequences associated with it as the true sequence. This is because the original starting NAOI will have generated a new PCR cycle counter sequence for each first-generation daughter sequence in every cycle of PCR. The parental NAOI is by definition the true sequence, and the possibility of the same error at the same position occurring multiple times for a given starting NAOI is low.

When conducting the sequence analysis part of the invention, the NAOI-originating components of the sequence reads may be mapped or aligned to a reference sequence. If target enrichment took place in the method, then the reference sequence will correspond to the target for which the reaction mixture was enriched. This greatly simplifies the analysis that must be undertaken.

To compare the NAOI sequences of the sequenced sample to each other and/or to a reference sequence, the sequences may be aligned (mapped) to each other and/or to a reference sequence; variation within the sequences can then be identified. Reads may be aligned to each other and/or to a reference sequence and analysed using bioinformatics software. Tools for mapping high-throughput sequencing data are reviewed by Fonseca et al., Bioinformatics. 2012 Dec. 15; 28(24):3169-77, the contents of which is incorporated herein in its entirety.

After alignment, differences can be identified between the sequences and/or between the sequences and a reference sequence (e.g. a reference genome sequence). To identify variation, sequences may be grouped by sequence similarity; such a comparison allows some mismatches and small structural variation (e.g. InDels) in sequence.

The methods of the invention allow a consensus sequence to be generated. A consensus sequence can be considered to be the most likely true sequence of the underlying NAOI. The determination of a consensus sequence may require individual starting molecules to be identified (for example using molecular barcoding techniques or using artificial break points in the NAOIs to infer separate starting molecules). When individual starting molecules are identified, the methods may comprise a step of grouping together sequence reads that originate (or are suspected of originating) from the same staring molecule. Grouping according to the PCR cycle counter sequences is still undertaken. A consensus sequence can be generated by identifying the modal nucleotide (i.e. the nucleotide that occurs with the highest frequency) at a given position in an individual NAOI.

In one embodiment of the invention, the method comprises grouping sequence reads to group together all sequence reads that originate (or are suspected of originating) from the same parental NAOI, sub-grouping the sequence reads according to the sequence of the PCR cycle counter, and for each nucleotide position, determining the nucleotide that is associated with the highest number of different PCR cycle counters. In this way, a consensus (i.e. true) sequence of the underlying NAOI can be determined and errors in the sequence reads can be corrected. Grouping sequence reads to group together all sequence reads that originate (or are suspected of originating) from the same parental NAOI may comprise grouping the sequence reads according to the sequence of a barcode.

Depending on the length of the sequence reads in the initial sequence run, it might be the case that not every initial sequence read includes the entirety of the PCR counter and the sequence of the nucleic acid of interest (and any barcode that may be present). For example, if the number of nucleotides making up the PCR counter, the sequence of the nucleic acid of interest and optional barcode is, for example, 200 nucleotides, but the first round of sequencing (determining the sequence of the forward strand) only sequences the first 150 base pairs, then not all of the sequences might be present in the initial sequence read. It may therefore be necessary to additionally sequence the reverse stand and, usually using a computer program, determine the complete sequence for the forward strand such that the final sequence read comprises the entire PCR counter, sequence of the nucleic acid of interest, and tag. Such methods are standard in the art. Hence references herein to sequence reads and libraries for analysis and/or error correction refer to the entire sequence (PCR counter, NAOI, and optional barcode and other components), and the skilled person would understand what steps are necessary to ensure the entire sequence is provided (for example, as determined by the length of the molecule being sequenced and the number of nucleotides sequenced in each sequence run).

In some embodiments of the invention, the sequence reads further comprise one or more index sequences that act as sample or replicate identifiers. For any given sequence read, the index sequence(s) is/are different to the sequence of the PCR counter, the nucleic acid of interest, and the optional molecular barcode. When two or more index sequences are present, the index sequences are generally different from each other. In some embodiments, all sequences originating from the same sample or replicate will share at least one common index sequence. The index sequences may have been introduced at any stage, for example as part of the original oligonucleotide or as part of a sequencing adaptor. Alternatively, they could have been separately ligated on to the NAOI. In some embodiments, the index sequence may have been introduced by primers used in a PCR amplification step.

In some embodiments of the invention, methods comprising determining the sequence of one or more NAOIs or cfDNA molecules comprises a step of determining a consensus sequence for the NAOI or cfDNA molecule(s). This may comprise grouping or aligning all sequence reads having the same barcode (when used) and obtaining a consensus sequence for that nucleic acid of interest. The sequence of the NAOI itself can also be used to help group the sequence reads according to individual starting molecules. For example, although barcode libraries are designed to have sufficient heterogeneity, the possibility of the same barcode being generated on two different starting NAOIs cannot be completely eliminated. However, the sequence of the NAOI itself can distinguish between two different starting NAOIs that have the same barcode tag.

A consensus sequence can be defined as a sequence occurring in at least 20%, at least 30%, at least 40%, at least 50%, at least 60%, at least 70%, at least 80% or at least 90% of all sequence reads for a single originating nucleic acid of interest. Preferably the sequence occurs in at least 20% of the sequence reads. Such a low threshold is possible in view of the additional information provided by the PCR cycle counter sequences, since even if a nucleotide is reported at a given nucleotide position in 20% of sequence reads, if it is associated with the largest number of different PCR cycle counter sequences, there is a higher probability the 20% nucleotide is correct.

"Consensus sequence" as used herein may refer to the sequence of the NAOI that is determined to be most likely sequence of the original NAOI. The nature of the amplification and sequencing steps means errors may be introduced into the resulting sequence read. The present invention allows error correction of the sequence read, and correcting such errors allows the skilled person to arrive at a "consensus sequence" as being the most likely sequence of the original NAOI. For example, the consensus sequence may be determined by the most commonly reported nucleic acid at a given position of the NAOI. When combined with techniques that allow individual starting molecules to be identified (for example when combining the invention with molecular barcoding techniques) and the sequence reads are grouped accordingly, even low allelic fraction mutations or other changes can be identified. Alternatively, the consensus sequence may be determined by the reported nucleic acid at a given position of the NAOI that is associated with the highest number of different PCR cycle counter sequences. In some embodiments, the consensus sequence may be determined with reference to both the relative frequency of each nucleotide reported at a given position, and the number of different PCR cycle counters associated with nucleotide reported at a given position.

Often, identification of the consensus sequence may be done by reference to a combination of the number of reads and the number of PCR counters. For example, if a consensus sequence cannot be determined solely by the number of reads originating from a parental NAOI, then reference can be made to the number of PCR counters to help reach a decision on (i.e. call) the consensus sequence. In one embodiment of the invention, the step of determining a consensus sequence requires determining the frequency with which a given sequence is present in the dataset of sequence reads and determining the number of different PCR counters associated with that sequence. A determination of the consensus sequence can then be made accordingly.

Consensus sequences may be determined on a nucleotide-by-nucleotide basis. The determination of a consensus sequence may therefore require consideration of the frequency of the identity of each nucleotide in a sequence, and the number of different PCR counter sequences associated with the identity of each nucleotide, rather than just considering each sequence read as a whole.

As mentioned, the method may additionally comprise a step of mapping the sequence reads to a reference genome. Generally the reference genome will be from the same species from which the NAOI originated. The step of mapping of the sequence reads to a reference genome may occur prior to grouping or aligning all sequence reads as discussed above. In some embodiments, the mapping of the sequence reads to a reference genome may occur after obtaining a consensus sequence.

The present invention also provides a method of counting sequencing reads comprising:
  a. providing a dataset comprising a plurality of sequence reads from a sample, each sequence read comprising a NAOI-originating component and a PCR cycle counter component, and optionally a barcode component;
  b. grouping sequence reads by the sequence of the PCR cycle counter, the NAOI-originating component and/or the barcode component; and
  c. counting the number of starting molecules to determine the copy number of the original NAOI.

The copy number of the original (originating) NAOI is the frequency with which a starting NAOI molecule occurred in the original sample. Therefore, in addition to cancer alterations resulting in changes in copy number, such methods may be useful in determining aneuploidy, such as fetal aneuploidy, using a sample obtained from a patient. Fetal aneuploidy can be determined using cell-free fetal DNA obtained from a maternal sample, in particular a maternal blood or plasma sample. The present invention therefore also provides method of determining the present of absence of aneuploidy, such as fetal aneuploidy, using methods described herein.

The present invention also provides a method of distinguishing between a genetic alteration, variation or mutation in a nucleic acid of interest and an error introduced during processing of said NAOI, the method comprising:
  a. providing a dataset comprising a plurality of sequence reads from a sample, each sequence read comprising a NAOI-originating component and a PCR cycle counter component, and optionally a barcode component;
  b. grouping sequence reads by the sequence of the PCR cycle counter, the NAOI-originating component and/or the barcode component; and
  c. correcting errors in the sequence reads to provide a consensus sequence for each originating nucleic acid of interest, thereby distinguishing between a genetic alteration, variation or mutation in a nucleic acid of interest and an error introduced by processing.

In some embodiments, step c) may comprise determining the number of different PCR counters associated with each NAOI and determining the consensus (i.e. true) sequence of the NAOI by keeping the sequence of the NAOI that is associated with the largest number of different PCR counters.

In some embodiments, the step of distinguishing true variants in parental NAOI sequence from false variants in parental NAOI sequence comprises grouping the sequence reads to group together sequence reads arising from the same starting NAOI, sub-grouping the sequence reads according to the PCR cycle counter sequence (or vice versa), and quantifying the relative amount of each different nucleotide reported at each position for each subgroup.

Reference Sequences

In some embodiments of the invention, the methods may comprise comparing the NAOI-originating portion of the sequence reads with a reference sequence or a database of reference sequences. The reference sequence may be a reference genome, reference gene, or a reference genomic region, or a database of reference genomes, reference genes, or reference genomic regions. The variants in parental NAOI sequence may be variants compared to the reference sequence or an entry in the database of reference sequences.

Typically a variant may differ from its reference sequence. However even if a given nucleotide base is the same as the reference sequence, this is still referred to as a "variant", for example a wild-type variant. The term "variant" herein refers to base calls made at the individual nucleotide base level.

Other Methods of the Invention

There is provided a method, comprising:
 a. providing a sample from a patient, said sample comprising one or more NAOIs; and
 b. sequencing one or more NAOIs according to a method of the invention.

The method may be a method of diagnosing cancer, a method of determining cancer prognosis, a method of determining cancer remission or relapse, a method of characterising cancer, a method of detecting progression of cancer, or a method of determining the presence or absence of residual cancer. The method may comprise extracting, isolating or enriching for the NAOI from the patient sample prior to sequencing the one or more NAOIs.

In one embodiment of the invention, there is provided a method of treating a disease, such as cancer, comprising
 a. providing a sample from a patient, said sample comprising one or more cell-free nucleic acid molecules of interest (NAOI);
 b. sequencing one or more NAOIs according to a method of the invention; and
 c. administering a therapy to the patient, such as a cancer therapy.

In one embodiment of the invention, there is provided a method of determining a treatment regimen for a patient, such as a cancer patient or a patient suspected of having cancer, comprising:
 a. providing a sample from a patient, said sample comprising one or more cell-free nucleic acid molecules of interest (NAOI);
 b. sequencing one or more NAOIs according to a method of the invention; and
 c. selecting a treatment regimen for the patient according to the sequence or sequences of the one or more NAOIs.

The method may further comprise administering said treatment regimen to the patient.

In one embodiment of the invention, there is provided a method of predicting a patient's responsiveness to a cancer treatment, comprising
 a. providing a sample from a patient, said sample comprising one or more cell-free nucleic acid molecules of interest (NAOI);
 b. sequencing one or more NAOIs according to a method of the invention;
 c. predicting a patient's responsiveness to a cancer treatment according to the sequence or sequences of the one or more NAOIs.

There is provided a method of testing for a disease, condition or organism, comprising:
 a. providing a sample from a patient, said sample comprising one or more cell-free nucleic acid molecules of interest (NAOI);
 b. sequencing one or more NAOIs according to a method of the invention; and
 c. determining the presence of absence of the disease, condition or organism by comparing the sequence and/or frequency of the nucleic acid of interest with a reference.

The invention also provides a method for testing for a disease, condition or organism, comprising, the method comprising:
 a. providing a NAOI labelled with a PCR cycle counter generator sequence attached (wherein the PCR cycle counter was generated using a method of the invention);
 b. amplifying the labelled nucleic acid of interest;
 c. determining the sequence and of the nucleic acid of interest; and
 d. determining the presence of absence of the disease, condition or organism by comparing the sequence of the nucleic acid of interest with a reference, e.g. a reference sequence.

The invention also provides a method for testing for a disease, condition or organism, comprising, the method comprising:
 a. providing an amplicon prepared by labelling and subsequent amplification of a NAOI according to a method of the invention as described herein;
 b. determining the sequence of the nucleic acid of interest; and
 c. determining the presence of absence of the disease, condition or organism by comparing the sequence of the nucleic acid of interest with a reference, e.g. a reference sequence.

The reference may be the sequence of a NAOI that is associated with the disease, condition or organism. The sample may be a patient sample or a sample obtained from the environment, for example the source of the sample is being tested for the presence of a particular organism.

The present invention also provides a method, comprising:
 a. obtaining a sample from a patient, said sample comprising a plurality NAOIs, optionally wherein the NAOIs are cell-free DNA (cfDNA) molecules; and
 b. determining the sequence of one or more of the NAOIs according to a method of the invention as described herein.

The methods of the invention may further comprise a step of determining the presence or absence of a NAOI in the sample, or the presence or absence of a genetic alteration (e.g., mutation or variant) in the nucleic acid of interest. The step of obtaining the sample may be a step of the method, or alternatively the method may be carried out using a sample previously obtained from a patient.

In further embodiments of the invention, the methods may comprise mapping the sequence reads to a reference genome.

Methods provided herein include a method of diagnosing cancer, a method of determining cancer prognosis, a method of determining cancer remission or relapse, a method of detecting progression of cancer, or a method of determining the presence or absence of residual cancer, wherein the cfDNA is circulating tumour DNA (ctDNA) and the method further comprises determining the presence or absence of a genetic alteration in the ctDNA. In such methods, the NAOI is contained within or derived from a patient sample. The sample may obtained from a patient that has, is suspected of having, or has had, cancer. Alternatively, there may be no reason to suspect the patient has cancer, since the present method may be used for early detection of cancer. The present invention therefore provides:
 (I) A method of diagnosing cancer or a method of detecting cancer mutations, comprising:

a. providing a sample from a patient, said sample comprising a plurality of cell-free DNA (cfDNA) molecules;
b. determining the sequence of one or more of the cfDNA molecules according to a method of the invention as described herein;
c. determining the presence or absence of one or more genetic alterations in the cfDNA molecules; and
d. determining the presence or absence of cancer or cancer mutations based on the presence or absence respectively of the one or more genetic alterations.

(II) A method of determining cancer remission or relapse, comprising:
a. providing a sample from a patient, said sample comprising a plurality of cell-free DNA (cfDNA) molecules;
b. determining the sequence of one or more of the cfDNA molecules according to a method of the invention as described herein;
c. determining the presence or absence of one or more genetic alterations in the cfDNA molecules; and
d. determining cancer remission or relapse based on the absence (or decrease in frequency of) or presence respectively of the one or more genetic alterations.

(III) A method of detecting progression of cancer, comprising:
a. providing a sample from a patient, said sample comprising a plurality of cell-free DNA (cfDNA) molecules;
b. determining the sequence of one or more of the cfDNA molecules according to a method of the invention as described herein;
c. determining the presence or absence of one or more genetic alterations in the cfDNA molecules, or determining a change in the abundance of the one or more genetic alterations;
d. optionally comparing the results from step (c) to the results for the same patient using a sample obtained at a previous point in time; and
d. determining a progression of cancer based on the presence or absence of the one or more genetic mutations, or based on a change in the abundance of the one of more genetic alterations.

(IV) A method of determining the presence of residual cancer, comprising:
a. providing a sample from a patient, said sample comprising a plurality of cell-free DNA (cfDNA) molecules;
b. determining the sequence of one or more of the cfDNA molecules according to a method of the invention as described herein;
c. determining the presence or absence of one or more genetic alterations in the cfDNA molecules; and
d. determining the presence of residual cancer based on the presence or absence of the one or more genetic alterations.

The above methods may be carried out on patients that are undergoing or have undergone cancer treatment. Alternatively, the above methods may be determinative in the treatment regimen for a cancer patient. For example, progression of cancer may be a worsening or improvement. If a worsening of cancer is detected, the patient may be treated with a different or more aggressive therapy. If a sufficient improvement is detected, treatment may be ended. To determine a progression of cancer, it may be possible to analyse only one sample from a patient. For example, a genetic alteration (such as a cancer mutation) may be detected that is indicative of late stage or aggressive cancer. Alternatively, the results may be compared with a sample obtained from the same patient at an early point in time. For example, the earlier sample may have been obtained from the same patient prior to onset or diagnosis of cancer. Alternatively, the earlier sample may have been obtained from the same patient prior to or at an earlier stage of treatment. In this way, the progression of cancer in a patient can be measured by carrying out an analysis on two or more samples obtained from a patient at different points in time.

There is therefore also provided a method of treating cancer, comprising treating a patient for cancer, wherein the patient has been determined as having cancer or at risk of a worsening of cancer or of cancer remission or relapse using a method of the invention.

In one embodiment, the method of treatment comprises:
a. providing a sample from a patient, said sample comprising a plurality of cell-free DNA (cfDNA) molecules;
b. determining the sequence of one or more of the cfDNA molecules according to a method of the invention as described herein;
c. determining the presence or absence of one or more genetic alterations in the cfDNA molecules;
d. selecting a cancer treatment regimen for the patient according to the presence or absence of a genetic alteration in the cell-free nucleic acid molecules; and
e. administering said cancer treatment regimen to the patient when one or more genetic alterations are detected.

Such a method may alternatively comprise:
a. determining the presence or absence of one or more genetic alterations in a library of sequence reads, the sequence reads having been obtained according to one of the methods of the invention described herein;
b. selecting a cancer treatment regimen for a patient according to the presence or absence of a genetic alteration in the cell-free nucleic acid molecules; and
c. administering said cancer treatment to the patient when one or more genetic alterations are detected.

The present invention also provides a method of determining a treatment regimen, such as a cancer treatment regimen, for a patient, for example a cancer patient or a patient suspected of having cancer, comprising:
a. providing a sample from a patient, said sample comprising a plurality of cell-free DNA (cfDNA) molecules;
b. determining the sequence of one or more of the cell-free nucleic acid molecules according to a method of the invention as described herein;
c. determining the presence or absence of a genetic alteration in the cell-free nucleic acid molecules; and
d. selecting a treatment regimen for the patient according to the presence or absence of a genetic alteration in the cell-free nucleic acid molecules.

Such a method may alternatively comprise:
a. determining the presence or absence of one or more genetic alterations in a library of sequence reads, the sequence reads having been obtained according to one of the methods described herein; and
b. selecting a treatment regimen for the patient according to the presence or absence of a genetic alteration in the library of sequence reads.

In some embodiments, the methods include the step of administering treatment.

In embodiments relating to treatment of diseases (such as cancer) or selecting a treatment regimen for a disease (such as cancer), the treatment may be based on the results of the genetic analysis. In some embodiments, the presence of a genetic alteration may be indicative of disease, or indicative of resistance or susceptibility to certain treatments. In some embodiments, the frequency of a genetic alteration may be indicative of disease, or indicative of resistance or susceptibility to certain treatments. In such embodiments, the method may further comprise the step of comparing the results of the genetic analysis to a reference (such as a healthy control or a control taken from the same patient at a different point in time). The skilled person would be able to interpret the results of the genetic analysis, depending on the context. Additionally or alternatively, the methods may include conducting an analysis on two or more samples obtained from the same patient at different points in time. In this way, disease progress and the success or failure of treatments can be monitored.

The present invention also provides a method of predicting a patient's responsiveness to a cancer treatment, comprising
a. providing a sample from a patient, said sample comprising a plurality of cell-free DNA (cfDNA) molecules;
b. determining the sequence of one or more of the cfDNA molecules according to a method of the invention as described herein;
c. determining the presence or absence of a genetic alteration; and
d. predicting a patient's responsiveness to a cancer treatment according to the presence or absence of a genetic alteration.

Such a method may alternatively comprise:
a. determining the presence or absence of one or more genetic alterations in a library of sequence reads, the sequence reads having been obtained according to one of the methods described herein; and
b. predicting a patient's responsiveness to a cancer treatment according to the presence or absence of a genetic alteration in the library of sequence reads.

The treatment to be administered may be chemotherapy, radiotherapy, targeted therapy and/or immunotherapy. The specific treatment regimen may depend on the type of cancer that is detected. For example, some genetic alterations (e.g., mutations) may be indicative of a particular resistance or susceptibility to certain treatments, and the treatment regimen can be designed accordingly.

The genetic alterations being detected are not limited in the present invention and are known and understood by the skilled person. Indeed, methods of the present invention can be used to detect new or existing genetic alterations and associate those alterations with particular cancers or particular patient outcomes, for example susceptibility or resistance to particular treatment regimens.

Generally, the type genetic alteration or genetic variation being detected will depend on the context. For example, an alteration, variation or mutation that affects the amount or activity of the gene or gene product, as compared to the normal or wild-type gene. The alteration can be in amount, structure, and/or activity in a diseased tissue or cell (e.g., cancer tissue or cell), as compared to its amount, structure, and/or activity, in a normal or healthy tissue or cell (e.g., a control), and is associated with a disease state, such as cancer. Alternatively, the genetic alteration might be indicative of a genetic disease.

An alteration might have an altered nucleotide sequence (e.g., a mutation), amino acid sequence, chromosomal translocation, intra-chromosomal inversion, copy number, expression level, protein level, protein activity, or methylation status, in a cancer tissue or cancer cell, as compared to a normal, healthy tissue or cell. Exemplary alterations include, but are not limited to, point mutations (e.g., silent, missense, or nonsense), deletions, insertions, inversions, linking mutations, duplications, translocations, inter- and intra-chromosomal rearrangements. Mutations can be present in the coding or non-coding region of the gene. In certain embodiments, the alteration(s) is detected as a rearrangement, e.g., a genomic rearrangement comprising one or more introns or fragments thereof (e.g., one or more rearrangements in the 5'- and/or 3'-UTR). In certain embodiments, the alterations are associated (or not associated) with a phenotype, e.g., a cancerous phenotype (e.g., one or more of cancer risk, cancer progression, cancer treatment or resistance to cancer treatment). In one embodiment, the alteration is associated with one or more of: a genetic risk factor for cancer, a positive treatment response predictor, a negative treatment response predictor, a positive prognostic factor, a negative prognostic factor, or a diagnostic factor.

Alterations and mutations may be or may occur in or at: a single nucleotide position; an intragenic region or an intergenic region; an exon or an intron, or a fragment thereof; a coding region or a non-coding region; a promoter; an enhancer, a 5' untranslated region (5' UTR), or a 3' untranslated region (3' UTR), or a fragment thereof; a cDNA or a fragment thereof; an SNP; a somatic mutation, a germ line mutation or both; a point or a single mutation; a deletion mutation; an in-frame deletion, an intragenic deletion, a full gene deletion; an insertion mutation; an intragenic insertion; an inversion mutation; an intra-chromosomal inversion; a linking mutation; a linked insertion mutation; an inverted duplication mutation; a tandem duplication; an intrachromosomal tandem duplication; a translocation; a chromosomal translocation, a non-reciprocal translocation; a rearrangement; a genomic rearrangement; a rearrangement of one or more introns, or a fragment thereof; a rearranged intron; or a combination thereof.

In embodiments of the invention relating to cancer, the genetic alteration will be a genetic cancer alteration, such as a cancer mutation, which is associated with cancer, or predictive of responsiveness or non-responsiveness to anti-cancer therapeutics.

Cancer progression is associated with accumulation of genetic alterations in cells. Alterations in tumor suppressor genes and oncogenes accumulate during tumor progression and may correlate with the clinical aggressiveness of cancer. A number of genes have been also identified that play a role in inducing or suppressing metastasis.

In one embodiment, methods of the invention can be used to target patient-specific mutations. As per, for example, Forshew et al., "Noninvasive identification and monitoring of cancer mutations by targeted deep sequencing of plasma DNA", 2012, *Sci Transl Med.*, May 30; 4(136):136ra68, a tumour or plasma sample from a patient is sequenced, for example using a broad method such as whole genome, exome or cancer panel sequencing. A capture panel targeting patient-specific somatic mutations identified during this sequencing can then be generated. Optionally, this capture panel can be combined with a non-patient-specific panel. Importantly the capture panel can include both driver and passenger mutations. A driver mutation is causally implicated in oncogenesis. It has conferred growth advantage on the cancer cell and has been positively selected in the microenvironment of the tissue in which the cancer arises. A driver mutation need not be required for maintenance of the final cancer. A passenger mutation has not contributed to cancer development. Passenger mutations are found within cancer genomes because somatic mutations without functional consequences often occur during cell division. Thus, a cell that acquires a driver mutation will already have biologically inert somatic mutations within its genome. These will be carried along in the clonal expansion that follows and therefore will be present in all cells of the final cancer.

The capture panel can then be used with the methods of the invention described herein to diagnose, monitor or characterise a cancer in a patient. By screening for a large number of mutations previously identified in the patient there is an improved ability to detect cancer DNA and a more accurate ability to quantify average levels, since even if the tumour evolves it is unlikely that it will lose all mutations. Equally, even if less than 1 copy of the cancer genome is analysed by screening for multiple changes, detection is still possible using the methods of the invention as the error correction aspect provides methods with significantly increased accuracy over the prior art.

Accordingly, in a further aspect of the invention there is provided a method of monitoring disease progression of cancer in an individual, said method comprising
(a) determining according to a method of the invention as described herein the presence or absence of one or more genetic alterations associated with a cancer in body fluid samples obtained from said individual at a plurality of time points following diagnosis of said individual with cancer;
(b) comparing the results obtained at each time point in order to determine the progression of the cancer in said individual; wherein the same or an increase in genetic alteration levels between samples taken at different time points indicates an increase in cancer burden, and wherein a decrease in cancer alteration levels between samples taken at different time points indicates cancer regression.

In one embodiment, the step of determining the presence or absence of one or more genetic alterations associated with cancer is carried out after initiation of treatment.

In some embodiments, the results are further compared with genetic alteration levels determined prior to initiation of treatment from an initial or primary sample of fluid or tissue obtained from the individual following diagnosis with cancer. For example, an initial genetic alteration profile may be established from a tumor tissue sample obtained from the individual and/or from a blood sample.

The methods of the present invention also allow detection of minimal residual disease in patients. For example, following treatment for cancer, the methods of the present invention may be used to detect residual disease using a sample obtained from the patient. The potential for relapse can therefore be detected early and appropriate additional treatment steps be taken.

There is also provided a method of stratifying a microbial population, comprising:
a. obtaining a sample comprising a plurality of microbial nucleic acids of interest;
b. determining the sequence of one or more of the microbial nucleic acids of interest according to a method of the invention as described herein;
c. mapping the sequence reads obtained in step b to a reference genome or genomes; and
d. stratifying the microbial population according to the identified microbes.

Kits

In a further aspect of the invention there is provided a kit of parts, comprising a pool of oligonucleotides of the invention, and optionally instructions for use. The instructions may be for a method of the invention as described herein.

The kit may also comprise one or more nucleotides in solution, for example, A, T, C and G nucleotides in solution. The oligonucleotides and nucleotides in solution are disposed in separate containers. In some embodiments, the different types of nucleotides are disposed in separate containers.

In some embodiments of the invention, the kit further comprises enzymatic means for ligation of nucleic acids. The enzymatic means for ligation of nucleic acids can be a ligase, for example a DNA ligase, such as T4 DNA ligase. The kit may also (or alternatively) comprise enzymatic means for polymerisation of nucleic acids. The enzymatic means for polymerisation of nucleic acids can be a polymerase, such as a DNA polymerase, for example Taq DNA polymerase.

In some embodiments of the invention, each component of the kit is disposed in separate container, with one container comprising the pool of adaptors and optionally the nucleotides in solution (or the nucleotides in solution may be in a container or containers separate to the pool of extension adaptors).

The present invention further provides a mixture or composition comprising a plurality of oligonucleotides of the invention (i.e. a pool of oligonucleotides) and one or more nucleic acids of interest. The one or more nucleic acids of interest may comprise 3' ligation moieties that are complementary to a 3' ligation moiety on the oligonucleotides. In some embodiments, the oligonucleotides are ligated to the nucleic acids of interest. The nucleic acids of interest may be from 25 to 100,000 base pairs in length, from 25 to 50,000 base pairs in length, from 25 to 10,000 base pairs in length, from 25 to 1000 base pairs in length, from 50 to 500 base pairs in length in length, from 100 to 250 base pairs in length, or from 100 to 200 base pairs in length. In some embodiments, the nucleic acids of interest are double-stranded, for example double-stranded cfDNA obtained from a patient. The cfDNA may be ctDNA.

In one embodiment of the invention, the method comprises:
a) providing a sample comprising double stranded NAOIs, wherein the double stranded NAOIs are double stranded cfDNA molecules derived from a patient sample;
b) ligating oligonucleotides to the NAOIs, wherein the oligonucleotides are a double-stranded oligonucleotides, wherein the first strand of each oligonucleotide comprises a sequencing adaptor, a PCR cycle counter generator that comprises one or more universal nucleotide bases and a ligation moiety at its 3' end, and wherein the second strand of each oligonucleotide comprises a sequencing adaptor, a sequence complementary to the PCR cycle counter and a ligation moiety at its 5' end;
c) conducting PCR using to amplify NAOIs with oligonucleotides attached;
d) enriching the sample using target-based enrichment, for example in-solution hybridisation;
e) performing a further PCR amplification on the enriched product;
f) sequencing the amplified library of NAOIs to provide a set of sequence reads, wherein each sequence read comprises a NAOI-originating component and a PCR cycle counter component; and g) distinguishing true variants in NAOI sequences from false variants in NAOI sequences.

Preferred features for the second and subsequent aspect of the invention are as provided for the first aspect of the invention, mutatis mutandis.

The invention will now be further illustrated by reference to specific examples, which are provided for reference and are not to be construed as limiting on the scope of the claims.

EXAMPLES

Example 1: Workflow without Enrichment 16,000 genomic input copies are made up to 50 µL by diluting in 10 mM Tris-HCl, pH 8. DNA is end repaired, 5' phosphorylated and 3' A-tailed using 31 µl NEBNext Ultra II End Prep Enzyme Mix and 71 µl NEBNext Ultra II End Prep Reaction Buffer in a total volume of 60 µL (NEBNext Ultra II DNA Library Prep Kit for Illumina (NEB: E76455)). Reagents are mixed by pipetting up and down 10 times. DNA is incubated on the thermocycler for 30 minutes at 20° C. followed by 30 minutes at 65° C., with the thermocycler lid temperature set to 75° C. Adapter ligation is performed by adding 301 µl NEBNext Ultra II Ligation Master mix, 1 µl NEBNext Ligation Enhancer and 2.5 µl Ligation adapters (stock concentration 90 µM). Samples are mixed by pipetting up and down 10 times. The reaction mixture is incubated on the thermocycler at 20° C. for 15 minutes with the thermocycler lid temperature switched off. At this stage samples can be stored at −20° C. overnight. A SPRI bead (Beckman Coulter) clean-up is performed at a 0.9× bead to sample ratio, following the manufacturers recommendations. DNA is eluted in 18 µl Tris-HCl pH 8. 16 µl of the eluate is recovered. The DNA is split into 4 reactions (4×4 µL). To each 4 µL DNA, 6.25 µl KAPA HIFI HS URACIL+ RM (Roche 07959052001), 0.25 µl primer (NEBNext i501 and i701 indexing primers mixed together at a final concentration of 50 µM of each primer. *See example PCR primer sequences below) and 2 µl nuclease free water are added. PCR amplification is performed using the following parameters: step1. 95° C. 3 min, step2. 98° C. 20 sec, step3. 62° C. 15 sec, step4. 72° C. 1 min, Cycle back to step2, 4 times for a total of 5 cycles, step5 72° C. 1 min, hold at 4° C. A SPRI bead (Beckman Coulter) clean-up is performed at a 0.9× bead to sample ratio, following the manufacturers recommendations. DNA is eluted in 18 µl Tris-HCl pH 8. Average library size is assessed using the Tapestation. The library is quantified using KAPA qPCR quantification, following the manufacturers recommendations (Roche: KK4873). The library is sequenced on the Next-Seq 500 illumina instrument, following the manufacturers recommendations.

Example 2: Workflow with Enrichment for Regions of Interest 16,000 genomic input copies are made up to 50 µL by diluting in 10 mM Tris-HCl, pH 8. DNA is end repaired, 5' phosphorylated and 3' A-tailed using 31 µl NEBNext Ultra II End Prep Enzyme Mix and 7 µl NEBNext Ultra II End Prep Reaction Buffer in a total volume of 60 (NEBNext Ultra II DNA Library Prep Kit for Illumina (NEB: E76455)). Reagents are mixed by pipetting up and down 10 times. DNA is incubated on the thermocycler for 30 minutes at 20° C. followed by 30 minutes at 65° C., with the thermocycler lid temperature set to 75° C. Adapter ligation is performed by adding 301 µl NEBNext Ultra II Ligation Master mix, 1 µl NEBNext Ligation Enhancer and 2.5 µl Ligation adapters (stock concentration 90 µM). Samples are mixed by pipetting up and down 10 times. The reaction mixture is incubated on the thermocycler at 20° C. for 15 minutes with the thermocycler lid temperature switched off. At this stage samples can be stored at −20° C. overnight. A SPRI bead (Beckman Coulter) clean-up is performed at a 0.9× bead to sample ratio, following the manufacturers recommendations. DNA is eluted in 18 µl Tris-HCl pH 8. 16 µl of the eluate is recovered. The DNA is split into 4 reactions (4×4 µL). To each 4 µL DNA, 6.25 µl KAPA HIFI HS URACIL+ RM (Roche 07959052001), 0.25 µl primer (NEBNext i501 and i701 indexing primers mixed together at a final concentration of 50 µM of each primer. *See example PCR primer sequences below)) and 2 µl nuclease free water are added. PCR amplification is performed using the following parameters: step1. 95° C. 3 min, step2. 98° C. 20 sec, step3. 62° C. 15 sec, step4. 72° C. 1 min, Cycle back to step2, 4 times for a total of 5 cycles, step5 72° C. 1 min, hold at 4° C. A SPRI bead (Beckman Coulter) clean-up is performed at a 0.9× bead to sample ratio, following the manufacturers recommendations. DNA is eluted in 18 µl Tris-HCl pH 8.

DNA is quantified using the Qubit fluorometer, following the manufacturers recommendations. Genomic DNA is enriched for regions of interest using xGen® Lockdown® probes and reagents form IDT, following the manufacturers recommendations. Average library size is assessed using the Tapestation. The library is quantified using KAPA qPCR quantification, following the manufacturers recommendations (Roche: KK4873). The library is sequenced on the Next-Seq 500 illumina instrument, following the manufacturers recommendations.

Example 3: Additional Workflow without a Molecular Barcode 1. cfDNA is extracted from Plasma (can be any type of DNA or RNA)
2. cfDNA is quantified (not necessary as part of invention)
3. DNA is "end-repaired"—mix of enzymes that blunt end the DNA
4. DNA is 5' phosphorylated
5. DNA is 3' A-tailed
6. Adapters (described in this invention) with 5' T-Tailed adapters are ligated to DNA (using T4 DNA ligase)
7. Bead based DNA clean-up is performed (SPRI Beads)
8. PCR primers directed against UPS are used to amplify DNA with adapters attached. This also adds Illumina sequences and sample indexes
9. Bead Based DNA Clean-up is performed (SPRI Beads)
10. PCR product is quantified (the sample could be sequenced at this point if enrichment is not necessary)
11. In-solution hybridisation is performed (using Probes against NAOI of interest)
12. Enriched product is amplified by PCR against illumina sequences added by PCR (step 8)
13. Library is quantified
14. Illumina sequencing is performed 2×150 bp Paired end sequencing Analysis:
1. Sample indexes are used to identify each sample and separate reads for that sample
2. Group reads based on sequence of NAOI
3. Group reads based on PCR cycle Counter
4. Error correct Example 4: Additional Workflow with a Molecular Barcode 1. cfDNA is extracted from Plasma (can be any type of DNA or RNA)
2. cfDNA is quantified (not necessary as part of invention)
3. DNA is "end-repaired"—mix of enzymes that blunt end the DNA
4. DNA is 5' phosphorylated
5. DNA is 3' A-tailed
6. Adapters (described in this invention) with 5' T-Tailed adapters are ligated to DNA (using T4 DNA ligase)
7. Bead based DNA clean-up is performed (SPRI Beads)
8. PCR primers directed against UPS are used to amplify DNA with adapters attached. This also adds Illumina sequences and sample indexes
9. Bead Based DNA Clean-up is performed (SPRI Beads)
10. PCR product is quantified (the sample could be sequenced at this point if enrichment is not necessary)
11. In-solution hybridisation is performed (using Probes against NAOI of interest)
12. Enriched product is amplified by PCR against illumina sequences added by PCR (step 8)
13. Library is quantified
14. Illumina sequencing is performed 2×150 bp Paired end sequencing Analysis
1. Sample indexes are used to identify each sample and separate reads for that sample
2. Group reads based on sequence of NAOI and molecular barcode
3. Group reads based on PCR cycle Counter
4. Generate consensus sequence Example PCR Primer Sequences I501:
(SEQ ID NO: 1)
AATGATACGGCGACCACCGAGATCTACAC<u>TATAGCCTA</u>CACTCTTTCCCT

ACACGACGCTCTTCCGATC*T

I701:
(SEQ ID NO: 2)
CAAGCAGAAGACGGCATACGAGAT<u>CGAGTAAT</u>GTGACTGGAGTTCAGACG

TGTGCTCTTCCGATC*T

Underlined: Illumina TruSeq HT index sequence, *phosphorothioate linkage

What is claimed is:

1. A method of sequencing nucleic acids of interest (NAOIs), comprising:
   a. providing a sample comprising parental NAOIs;
   b. attaching oligonucleotides to the parental NAOIs to provide labelled parental NAOIs, wherein the oligonucleotides comprise a PCR cycle counter generator sequence comprising at least one universal nucleotide base;
   c. amplifying the labelled parental NAOIs using PCR, wherein each cycle of the PCR amplification generates a new PCR cycle counter every time a labelled parental NAOI is copied by a polymerase, to provide an amplified library of daughter NAOIs each containing a PCR cycle counter sequence;
   d. sequencing the amplified library of daughter NAOIs to provide a set of sequence reads, wherein each sequence read comprises a NAOI-originating component and a PCR cycle counter component; and
   e. distinguishing true variants in parental NAOI sequences from false variants in parental NAOI sequences by counting the number of different PCR cycle counter sequences.

2. The method of claim 1, wherein the oligonucleotides are double stranded oligonucleotides comprising a first and a second strand, the first strand comprising a sequencing adaptor, a PCR cycle counter generator sequence and a 3' ligation moiety, and the second strand comprising a sequencing adaptor, a region complementary to the PCR cycle counter generator sequence, and a 5' ligation moiety.

3. The method of claim 2, wherein amplification by PCR uses primers directed towards the oligonucleotides attached in step (b).

4. The method of claim 1, further comprising comparing the NAOI-originating portion of the sequence reads with a reference sequence or a database of reference sequences.

5. The method of claim 4, wherein the reference sequence is a reference genome, reference gene, or a reference genomic region, or wherein the database of reference sequences is a database of reference genomes, reference genes, or reference genomic regions.

6. The method of claim 4, wherein the variants in parental NAOI sequence are variants compared to the reference sequence or an entry in the database of reference sequences.

7. The method of claim 6, wherein the larger the number of different PCR cycle counter sequences associated with each different NAOI-originating component or portion thereof, the higher probability there is of the variant being a true variant.

8. The method of claim 1, wherein distinguishing true variants in parental NAOI sequence from false variants in parental NAOI sequence comprises quantifying the relative amount of each different PCR cycle counter sequence for a given NAOI sequence.

9. The method of claim 1, wherein distinguishing true variants in parental NAOI sequence from false variants in parental NAOI sequence comprises comparing the number of PCR cycle counter sequences associated with each different NAOI-originating portion with the number of PCR cycles performed in step (c).

10. The method of claim 9, wherein when the number of different PCR cycle counter sequences associated with a given NAOI-originating portion is greater than the number of PCR cycles performed, this is indicative of the presence of a true variant.

11. The method of claim 1, further comprising tagging the parental NAOIs prior to amplification with a molecular barcode.

12. The method of claim 11, wherein the oligonucleotides comprise the molecular barcode.

13. The method of claim 11, wherein distinguishing true variants in a parental NAOI sequence from false variants in a parental NAOI sequence comprises:
a) grouping the sequence reads according to the sequence of the molecular barcode and optionally the sequence of the NAOI-originating component to group together all sequence reads arising from the same parental NAOI molecule; and
b) counting the number of different PCR cycle counter sequences associated each different sequence of NAOI-originating component in the sequence reads.

14. The method of claim 13, wherein the NAOI-originating portion sequence having the highest number of different PCR cycle counter sequences associated with it is identified as the true parental NAOI sequence.

15. The method of claim 11, further comprising:
a) grouping the sequence reads according to the sequence of the molecular barcode and optionally the sequence of the NAOI-originating component to group together all sequence reads arising from the same parental NAOI;
b) aligning the sequence reads according to the sequence of the NAOI-originating portion; and
c) determining a consensus sequence for the parental NAOI, wherein the consensus sequence represents the sequence with the highest probability of being the true sequence of the parental NAOI, comprising identifying any nucleotide in the NAOI-originating portion of a sequence read for which more than one type of nucleotide is reported in a group of aligned sequence reads and counting the number of different PCR cycle counter sequences associated with each reported nucleotide.

16. The method of claim 15, further comprising selecting the nucleotide that is associated with the largest number of different PCR cycle counter sequences for the consensus sequence.

* * * * *